United States Patent
McKay

(10) Patent No.: US 8,470,360 B2
(45) Date of Patent: Jun. 25, 2013

(54) DRUG DEPOTS HAVING DIFFERENT RELEASE PROFILES FOR REDUCING, PREVENTING OR TREATING PAIN AND INFLAMMATION

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 568 days.

(21) Appl. No.: 12/105,994

(22) Filed: Apr. 18, 2008

(65) Prior Publication Data

US 2009/0263441 A1    Oct. 22, 2009

(51) Int. Cl.
*A61F 2/00* (2006.01)
*A61K 9/00* (2006.01)

(52) U.S. Cl.
CPC .................................. *A61K 9/0024* (2013.01)
USPC ........................................................ 424/426

(58) Field of Classification Search
None
See application file for complete search history.

(56) References Cited

U.S. PATENT DOCUMENTS

| | | |
|---|---|---|
| 3,190,802 A | 6/1965 | Zeile et al. |
| 3,020,660 A | 8/1965 | Zeile et al. |
| 4,765,974 A | 8/1988 | Tokuda et al. |
| 5,175,052 A | 12/1992 | Tokuda et al. |
| 5,447,947 A | 9/1995 | Campbell |
| 5,484,607 A | 1/1996 | Horacek |
| 5,635,204 A | 6/1997 | Gevirtz et al. |
| 5,752,390 A | 5/1998 | Hyde |
| 5,801,188 A | 9/1998 | Hassenbusch, III et al. |
| 5,869,100 A | 2/1999 | Horacek |
| 5,942,503 A | 8/1999 | Jung et al. |
| 5,942,530 A | 8/1999 | Panetta et al. |
| 5,945,416 A | 8/1999 | Shannon et al. |
| 5,980,927 A | 11/1999 | Nelson et al. |
| 6,030,642 A | 2/2000 | Horacek |
| 6,147,102 A | 11/2000 | Borgman |
| 6,165,486 A * | 12/2000 | Marra et al. ............... 424/423 |
| 6,231,885 B1 | 5/2001 | Carrara |
| 6,417,184 B1 | 7/2002 | Ockert |
| 6,534,048 B1 | 3/2003 | Borgman |
| 6,551,290 B1 | 4/2003 | Elsberry et al. |
| 6,571,125 B2 | 5/2003 | Thompson |
| 6,594,880 B2 | 7/2003 | Elsberry |
| 6,641,831 B1 | 11/2003 | Schierholz |
| 6,689,121 B1 | 2/2004 | Cafferata |
| 6,913,760 B2 * | 7/2005 | Carr et al. ............... 424/422 |
| 6,992,110 B2 | 1/2006 | Kranzler et al. |
| 7,045,543 B2 | 5/2006 | Yatvin et al. |

(Continued)

FOREIGN PATENT DOCUMENTS

| | | |
|---|---|---|
| WO | 0143726 A1 | 6/2001 |
| WO | 0143749 A2 | 6/2001 |

(Continued)

OTHER PUBLICATIONS

Wikipedia, "Majority" definition, p. 1.*

(Continued)

*Primary Examiner* — Bethany Barham
(74) *Attorney, Agent, or Firm* — Sorell Lenna & Schmidt LLP

(57) ABSTRACT

Effective treatments of pain and/or inflammation are provided. Through the administration of an effective amount of at least analgesic and/or at least one anti-inflammatory agent at or near a target site, one can reduce, prevent or treat inflammation and pain.

16 Claims, 6 Drawing Sheets

U.S. PATENT DOCUMENTS

| | | | |
|---|---|---|---|
| 7,067,144 B2 | 6/2006 | Demopulos et al. | |
| 7,074,426 B2 | 7/2006 | Kochinke | |
| 7,122,204 B2 | 10/2006 | Rudnic | |
| 7,282,221 B2 | 10/2007 | Rudnic et al. | |
| 7,314,939 B2 | 1/2008 | Pandey et al. | |
| 7,335,314 B2 | 2/2008 | Wu et al. | |
| 7,345,065 B2 | 3/2008 | Gil et al. | |
| 7,507,398 B2 | 3/2009 | Rabinowitz et al. | |
| 7,524,812 B2 | 4/2009 | Ellis et al. | |
| 2002/0058656 A1 | 5/2002 | Ockert | |
| 2002/0090398 A1* | 7/2002 | Dunn et al. | 424/486 |
| 2002/0094998 A1 | 7/2002 | Burke et al. | |
| 2002/0131988 A1* | 9/2002 | Foster et al. | 424/422 |
| 2002/0169162 A1 | 11/2002 | Smith et al. | |
| 2003/0009145 A1 | 1/2003 | Struijker-Boudier et al. | |
| 2003/0022926 A1 | 1/2003 | Lavand'Homme | |
| 2003/0152637 A1 | 8/2003 | Chasin et al. | |
| 2004/0001889 A1 | 1/2004 | Chen et al. | |
| 2004/0022859 A1 | 2/2004 | Chen et al. | |
| 2004/0028726 A1 | 2/2004 | Fischer et al. | |
| 2004/0101582 A1 | 5/2004 | Wolicki | |
| 2004/0109893 A1 | 6/2004 | Chen et al. | |
| 2004/0110893 A1* | 6/2004 | Matyjaszewski et al. | 524/556 |
| 2004/0151753 A1 | 8/2004 | Chen et al. | |
| 2004/0208917 A1 | 10/2004 | Fischer et al. | |
| 2004/0265364 A1 | 12/2004 | Ozturk et al. | |
| 2005/0058696 A1 | 3/2005 | Donello et al. | |
| 2005/0059744 A1 | 3/2005 | Donello et al. | |
| 2005/0069591 A1* | 3/2005 | Bernstein et al. | 424/489 |
| 2005/0095246 A1 | 5/2005 | Shafer | |
| 2005/0095277 A1 | 5/2005 | Ozturk et al. | |
| 2005/0112198 A1* | 5/2005 | Challapalli et al. | 424/464 |
| 2005/0244466 A1* | 11/2005 | Whitcup et al. | 424/427 |
| 2005/0245905 A1 | 11/2005 | Schmidt et al. | |
| 2006/0009478 A1 | 1/2006 | Friedmann et al. | |
| 2006/0165800 A1 | 7/2006 | Chen et al. | |
| 2006/0264509 A1 | 11/2006 | Fraser et al. | |
| 2007/0037891 A1 | 2/2007 | Esfand et al. | |
| 2007/0184084 A1 | 8/2007 | Chen et al. | |
| 2007/0196415 A1 | 8/2007 | Chen et al. | |
| 2007/0292475 A1 | 12/2007 | Campbell et al. | |
| 2007/0298074 A1* | 12/2007 | Robinson et al. | 424/427 |
| 2008/0057131 A1 | 3/2008 | Dasch et al. | |
| 2008/0152709 A1 | 6/2008 | Bortz | |
| 2008/0171075 A1 | 7/2008 | Ozturk et al. | |

FOREIGN PATENT DOCUMENTS

| | | |
|---|---|---|
| WO | WO2005009408 A2 | 2/2005 |
| WO | 2006011915 A1 | 2/2006 |
| WO | 2006022611 A2 | 3/2006 |
| WO | 2006101540 A1 | 9/2006 |
| WO | WO2007041410 A2 | 4/2007 |
| WO | 2008079868 A1 | 7/2008 |
| WO | 2009100441 A2 | 8/2009 |

OTHER PUBLICATIONS

"Pressure Conversion Table" from Transtronics (http://wiki.xtronics.com/index.php/Pressure_Conversion_Table) retrieved online on Jan. 26, 2012 (pp. 1-7).*

Seo, S.-A. et al., "A local delivery system for fentanyl based on biodegradable poly(L-lactide-co-glycolide) oligomer". Int. J. Pharm., 2002, vol. 239, pp. 93-101. See abstract; table 1; figures 2-5; conclusion.

International Search Report and Written Opinion for International Application No. PCT/US2009/040240 mailed on Oct. 20, 2009.

Hickey T et al: "Dexamethasone/PLGA microspheres for continuous delivery of an anti-inflammatory drug for implantable medical devices", Biomaterials, Elsevier Science Publishers BV., Barking, GB, vol. 23, No. 7, Apr. 1, 2002, pp. 1649-1656, XP004348175, ISSN: 0142-9612, DOI: 10.1016/S0142-0612(01)00291-5, abstract, p. 1655, paragraph 5.

International Search Report and Written Opinion for US/PCT/2009/040240 the counterpart application mailed on Oct. 17, 2011, 7 pages.

* cited by examiner

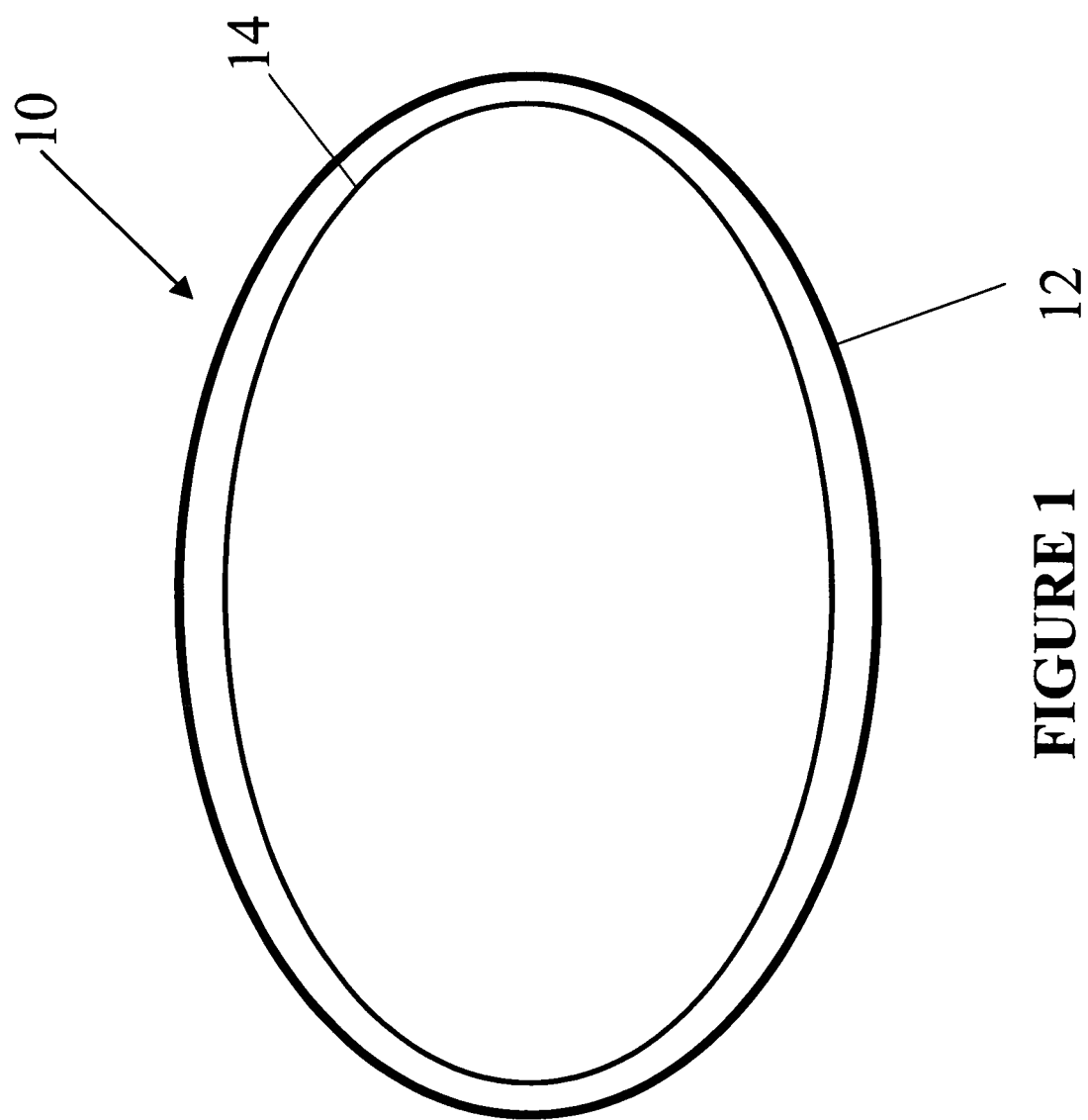

DRUG DEPOTS HAVING DIFFERENT RELEASE PROFILES FOR REDUCING, PREVENTING OR TREATING PAIN AND INFLAMMATION

BACKGROUND

Pain can adversely affect patients in many different ways. It can keep the patient from being active, sleeping well, enjoying family and friends, and from eating. Pain can make the patient feel afraid or depressed and prevent full participation in general rehabilitation programs and may even slow recovery.

Proper pain control is of prime importance to anyone treating many different diseases or conditions. Proper pain relief imparts significant physiological and psychological benefits to the patient. Not only does effective pain relief mean a smoother more pleasant recovery (e.g., mood, sleep, quality of life, etc.) with earlier discharge from medical/surgical/outpatient facilities, but it may also reduce the onset of chronic pain syndromes (e.g., fibromyalgia, myalgia, etc.).

Pain serves the important biological function of signaling the presence of damage or disease within the body and is often accompanied by inflammation (redness, swelling, and/or burning). There are two categories of pain: acute pain and neuropathic pain. Acute pain refers to pain experienced when tissue is being damaged or is damaged. Acute pain serves at least two physiologically advantageous purposes. First, it warns of dangerous environmental stimuli (such as hot or sharp objects) by triggering reflexive responses that end contact with the dangerous stimuli. Second, if reflexive responses do not avoid dangerous environmental stimuli effectively, or tissue injury or infection otherwise results, acute pain facilitates recuperative behaviors. For example, acute pain associated with an injury or infection encourages an organism to protect the compromised area from further insult or use while the injury or infection heals. Once the dangerous environmental stimulus is removed, or the injury or infection has resolved, acute pain, having served its physiological purpose, ends. As contrasted to acute pain, in general, neuropathic pain serves no beneficial purpose. Neuropathic pain results when pain associated with an injury or infection continues in an area once the injury or infection has resolved.

There are many painful diseases or conditions that require proper pain and/or inflammation control, including but not limited to rheumatoid arthritis, osteoarthritis, a spinal disc herniation (i.e., sciatica), carpal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, spondilothesis, stenosis, discogenic back pain, and joint pain or the like.

One particularly painful disease is sciatica. Sciatica is a chronic disease that often can be very debilitating and may take a terrible toll on those with the disease as well as their families, friends and caregivers. Sciatica is a very painful disease associated with the sciatic nerve, which runs from the lower part of the spinal cord (the lumbar region), down the back of the leg and to the foot. Sciatica generally begins with a herniated disc, which later leads to local immune system activation. The herniated disc also may damage the nerve root by pinching or compressing it, leading to additional immune system activation in the area.

Another particularly painful disease is spinal stenosis, where there is progressive constriction of the spinal canal and as it narrows, the nerve elements that reside within it become progressively more crowded. Eventually, the canal dimensions become sufficiently small—so as to significantly compress the nerve elements and produce pain, weakness, sensory changes, clumsiness and other manifestation of nervous system dysfunction. The disease causes lower back pain, lower extremity pain, lower extremity weakness, limitation of mobility and the high disability rates that often afflict the elderly.

Spondylolisthesis is another painful disease. Spondylolisthesis is a displacement disorder of the lumbar or cervical spine, in which one vertebral body is forwardly displaced over another vertebral body. Spondylolisthesis may be caused by a traumatic event or by degeneration of the spine. At times, the displacement disorder is accompanied by or caused by a fracture or partial collapse of one or more vertebrae or degeneration of a disc in the spine. Patients who suffer from such conditions can experience moderate to severe distortion of the thoracic skeletal structure, diminished ability to bear loads, loss of mobility, extreme and debilitating pain, and oftentimes suffer neurological deficits in nerve function.

There has been considerable interest in developing effective treatments for these painful diseases, yet to date current treatments are only partially effective.

SUMMARY

Compositions and methods are provided comprising an analgesic and/or an anti-inflammatory agent that are administered in order to treat pain and/or inflammation. The pain and/or inflammation may for example be due to chronic conditions including rheumatoid arthritis, osteoarthritis, a spinal disc herniation (e.g., sciatica), carpal/tarsal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, spondilothesis, stenosis, discogenic back pain, and joint pain or the like.

One advantage of the embodiments provided herein is that they utilize one or more drug depots or one or more drug depot regions having a different release profile for the therapeutic agent, which aids in the reduction, prevention or treatment of different diseases.

In various embodiments, one or more regions of the drug depot or one or more drug depots may be designed to release an initial burst or bolus dose of the analgesic and/or an anti-inflammatory agent, which provides initial relief in treatment of diseases (e.g., sciatica, spondilothesis, stenosis, etc.), while sustained release regions or drug depots provide sustained release of the therapeutic agent over a longer period of time. In this way more effective treatments for different diseases or conditions.

In one embodiment, an implantable drug depot is provided useful for reducing, preventing or treating pain and/or inflammation in a patient in need of such treatment, the implantable drug depot comprising a therapeutically effective amount of an analgesic and/or an anti-inflammatory agent, the depot being implantable at a site beneath the skin to reduce, prevent or treat pain and/or inflammation, wherein the drug depot comprises (i) at least one region capable of releasing a therapeutically effective bolus amount of the analgesic and/or the anti-inflammatory agent at a site beneath the skin; and (ii) at least one region capable of releasing a therapeutically effective amount of the analgesic and/or the anti-inflammatory agent over a period of at least three days.

In another embodiment, a kit is provided comprising a plurality of implantable drug depots useful for reducing, preventing or treating pain and/or inflammation in a patient in need of such treatment, the kit comprising a first set of the plurality of drug depots capable of releasing a therapeutically effective bolus amount of an analgesic and/or an anti-inflammatory agent or pharmaceutically acceptable salts thereof at a site beneath the skin and a second set of the plurality of drug depots capable of releasing a therapeutically effective amount of the analgesic and/or the anti-inflammatory agent or pharmaceutically acceptable salts thereof over a period of at least three days. In various embodiments, by implanting different sets of drug depot with different release profiles, the need to develop one set of drug depots with the desired immediate release and sustained release properties is avoided.

In one exemplary embodiment, a method of reducing, preventing or treating pain and/or inflammation in a patient in need of such treatment is provided, the method comprising administering a plurality of implantable drug depots at or near a target tissue site of the patient, wherein a first set of the plurality of drug depots is capable of releasing a therapeutically effective bolus amount of an analgesic and/or an anti-inflammatory agent or pharmaceutically acceptable salts thereof at a site beneath the skin and a second set of the plurality of drug depots is capable of releasing a therapeutically effective amount of the analgesic and/or the anti-inflammatory agent or pharmaceutically acceptable salts thereof over a period of at least three days.

In another exemplary embodiment, a plurality of implantable drug depots is proved that are useful for reducing, preventing or treating pain and/or inflammation in a patient in need of such treatment, the plurality of drug depots comprising a first set of one or more drug depots capable of releasing a therapeutically effective bolus dose of an analgesic and/or an anti-inflammatory agent or pharmaceutically acceptable salts thereof at a site beneath the skin and a second set of one or more drug depots capable of releasing a therapeutically effective amount of the analgesic and/or the anti-inflammatory agent or pharmaceutically acceptable salts thereof over a period of at least three days.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE FIGURES

In part, other aspects, features, benefits and advantages of the embodiments will be apparent with regard to the following description, appended claims and accompanying drawings where:

FIG. 1 is a schematic drawing illustrating an embodiment of one drug depot composition having a first region or layer capable of releasing a therapeutically effective bolus amount of the analgesic and/or the anti-inflammatory agent and a second region capable of releasing a therapeutically effective amount of the analgesic and/or the anti-inflammatory agent over a longer period of time.

Figure 1A:
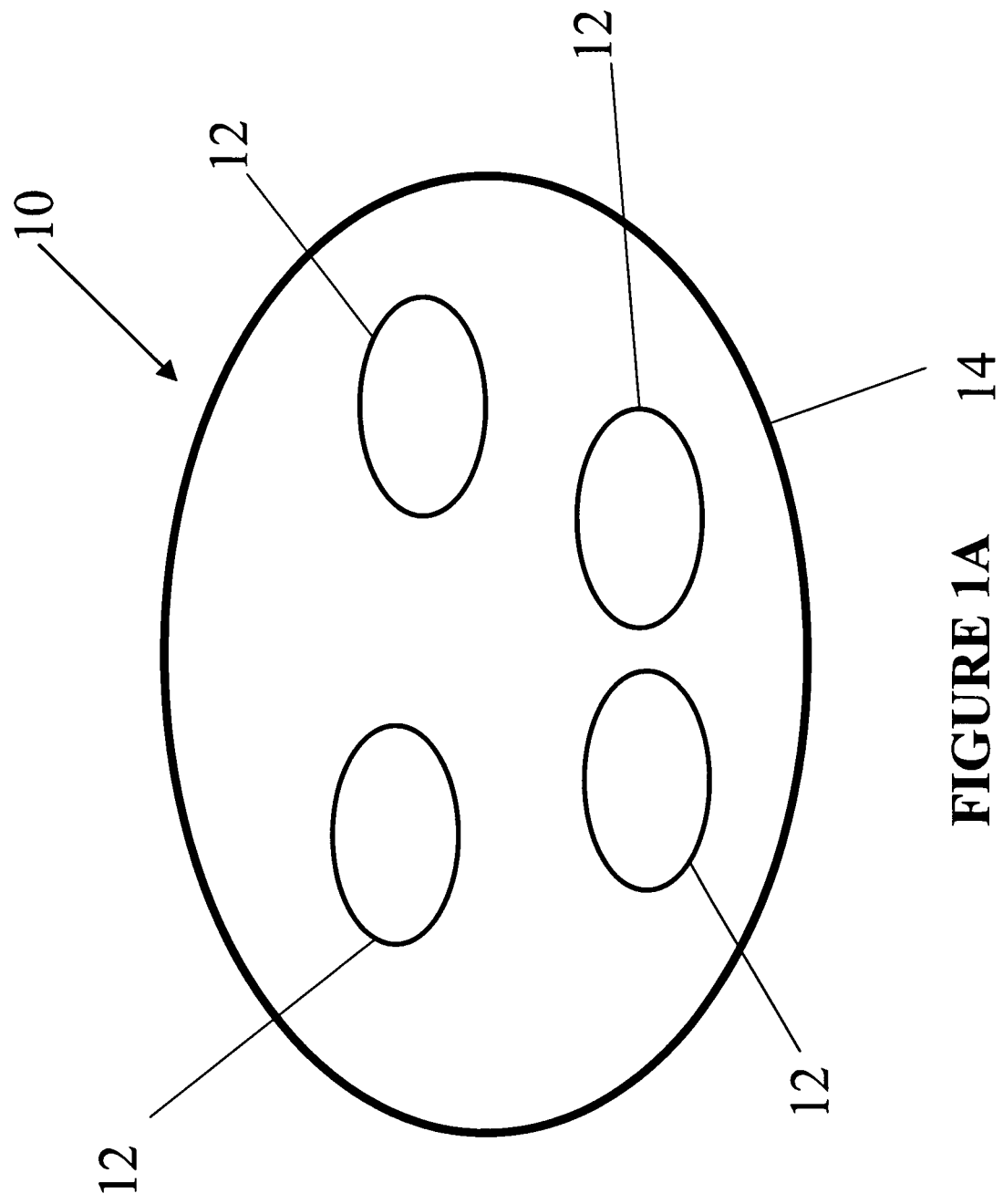
FIG. 1A is a schematic drawing illustrating an embodiment of one drug depot composition having a plurality of regions capable of releasing a therapeutically effective bolus amount of the analgesic and/or the anti-inflammatory agent and a region capable of releasing a therapeutically effective amount of the analgesic and/or the anti-inflammatory agent over a longer period of time.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

The headings below are not meant to limit the disclosure in any way; embodiments under any one heading may be used in conjunction with embodiments under any other heading.

DEFINITIONS

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

Analgesic refers to an agent or compound that can reduce, relieve or eliminate pain. Examples of analgesic agents include but are not limited to acetaminophen, a local anesthetic, such as for example, lidocaine, bupivicaine, ropivacaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, levorphanol, mepiridine, methadone, morphine, nalbuphine, opium, oxycodone, papaveretum, pentazocine, pethidine, phenoperidine, piritramide, dextropropoxyphene, remifentanil, sufentanil, tilidine, tramadol, codeine, dihydrocodeine, meptazinol, dezocine, eptazocine, flupirtine or a combination thereof.

The phrase "anti-inflammatory agent" refers to an agent or compound that has anti-inflammatory effects. These agents may remedy pain by reducing inflammation. Examples of anti-inflammatory agents include, but are not limited to, a statin, sulindac, sulfasalazine, naroxyn, diclofenac, indomethacin, ibuprofen, flurbiprofen, ketoprofen, aclofenac, aloxiprin, aproxen, aspirin, diflunisal, fenoprofen, mefenamic acid, naproxen, phenylbutazone, piroxicam, meloxicam, salicylamide, salicylic acid, desoxysulindac, tenoxicam, ketorolac, clonidine, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, triflumidate, fenamates (mefenamic acid, meclofenamic acid), nabumetone, celecoxib, etodolac, nimesulide, apazone, gold, tepoxalin; dithiocarbamate, or a combination thereof. Anti-inflammatory agents also include other compounds such as steroids, such as for example, fluocinolone, cortisol, cortisone, hydrocortisone, fludrocortisone, prednisone, prednisolone, methylprednisolone, triamcinolone, betamethasone, dexamethasone, beclomethasone, fluticasone interleukin-1 receptor antagonists, thalidomide (a TNF-α release inhibitor), thalidomide analogues (which reduce TNF-α production by macrophages), bone morphogenetic protein (BMP) type 2 or BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), guanidinoethyldisulfide, or a combination thereof.

Exemplary anti-inflammatory agents include, for example, naproxen; diclofenac; celecoxib; sulindac; diflunisal; piroxicam; indomethacin; etodolac; meloxicam; ibuprofen; ketoprofen; r-flurbiprofen; mefenamic; nabumetone; tolmetin, and sodium salts of each of the foregoing; ketorolac bromethamine; ketorolac tromethamine; ketorolac acid; choline magnesium trisalicylate; rofecoxib; valdecoxib; lumiracoxib; etoricoxib; aspirin; salicylic acid and its sodium salt; salicylate esters of alpha, beta, gamma-tocopherols and tocotrienols (and all their d, 1, and racemic isomers); methyl, ethyl, propyl, isopropyl, n-butyl, sec-butyl, t-butyl, esters of acetylsalicylic acid; tenoxicam; aceclofenac; nimesulide; nepafenac; amfenac; bromfenac; flufenamate; phenylbutazone, or a combination thereof.

Exemplary steroids include, for example, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, dexamethasone 21-acetate, dexamethasone 21-phosphate di-Na salt, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide or a combination thereof.

Examples of a useful statin for treatment of pain and/or inflammation include, but is not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448,784 and 4,450,171 these entire disclosures are herein incorporated by reference), fluvastatin, lovastatin, rosuvastatin and fluindostatin (Sandoz XU-62-320), dalvastain (EP Appln. Publn. No. 738510 A2, the entire disclosure is herein incorporated by reference), eptastatin, pitavastatin, or pharmaceutically acceptable salts thereof or a combination thereof. In various embodiments, the statin may comprise mixtures of (+)R and (−)-S enantiomers of the statin. In various embodiments, the statin may comprise a 1:1 racemic mixture of the statin.

Anti-inflammatory agents also include those with anti-inflammatory properties, such as, for example, amitriptyline, carbamazepine, gabapentin, pregabalin, clonidine, or a combination thereof.

Unless otherwise specified or apparent from context, where this specification and the set of claims that follows refer to an anti-inflammatory agent, the inventors are also referring to a pharmaceutically acceptable salt of the anti-inflammatory agent including stereoisomers. Pharmaceutically acceptable salts include those salt-forming acids and bases that do not substantially increase the toxicity of the compound. Some examples of potentially suitable salts include salts of alkali metals such as magnesium, calcium, sodium, potassium and ammonium, salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, or the like.

Similarly, when referring to an analgesic agent, unless otherwise specified or apparent from context, it is understood that the inventors are also referring to pharmaceutically acceptable salts including steroisomers. Pharmaceutically acceptable salts include those salt-forming acids and bases that do not substantially increase the toxicity of the compound. Some examples of potentially suitable salts include salts of alkali metals such as magnesium, calcium, sodium, potassium and ammonium, salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, or the like.

A "drug depot" is the composition in which at least one anti-inflammatory agent and at least one analgesic agent or the pharmaceutically acceptable salts of either or both are administered to the body. Thus, a drug depot may comprise a physical structure to facilitate implantation and retention in a desired site (e.g., a disc space, a spinal canal, a tissue of the patient, particularly at or near a site of surgery, pain, or site of inflammation, etc.). The drug depot also comprises the drug itself. The term "drug" as used herein is generally meant to refer to any substance that alters the physiology of a patient. The term "drug" may be used interchangeably herein with the terms "therapeutic agent," "therapeutically effective amount," and "active pharmaceutical ingredient" or "API." It will be understood that unless otherwise specified a "drug" formulation may include more than one therapeutic agent, wherein exemplary combinations of therapeutic agents include a combination of two or more drugs. The drug provides a concentration gradient of the therapeutic agent for delivery to the site. In various embodiments, the drug depot provides an optimal drug concentration gradient of the therapeutic agent at a distance of up to about 0.1 cm to about 5 cm from the implant site, and comprises at least one anti-inflammatory agent or its pharmaceutically acceptable salt and at least one analgesic agent or its pharmaceutically acceptable salt.

A "depot" includes but is not limited to capsules, microspheres, microparticles, microcapsules, microfibers particles, nanospheres, nanoparticles, coating, matrices, wafers, pills, pellets, emulsions, liposomes, micelles, gels, or other pharmaceutical delivery compositions or a combination thereof. Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof.

A "therapeutically effective amount" or "effective amount" is such that when administered, the drug results in alteration of the biological activity, such as, for example, inhibition of inflammation, reduction or alleviation of pain, improvement in the condition through muscle relaxation, etc. The dosage administered to a patient can unless otherwise specified or apparent from context be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. In some embodiments the formulation is designed for immediate release. In other embodiments the formulation is designed for sustained release. In other embodiments, the formulation comprises one or more immediate release surfaces and one or more sustain release surfaces.

The phrases "sustained release" or "sustain release" (also referred to as extended release or controlled release) are used herein to refer to one or more therapeutic agent(s) that is introduced into the body of a human or other mammal and continuously or continually releases a stream of one or more therapeutic agents over a predetermined time period and at a therapeutic level sufficient to achieve a desired therapeutic effect throughout the predetermined time period. Reference to a continuous or continual release stream is intended to encompass release that occurs as the result of biodegradation in vivo of the drug depot, or a matrix or component thereof, or as the result of metabolic transformation or dissolution of the therapeutic agent(s) or conjugates of therapeutic agent(s). As persons of ordinary skill are aware, sustained release formulations may, by way of example, be created as films, slabs, pellets, microparticles, microspheres, microcapsules, spheroids, shaped derivatives and paste. The formulations may be in a form that is suitable for suspension in isotonic saline, physiological buffer or other solution acceptable for injection into a patient. Further, the formulations may be used in conjunction with any implantable, insertable or injectable system that a person of ordinary skill would appreciate as useful in connection with embodiments herein including but not limited to parenteral formulations, microspheres, microcapsules, gels, pastes, implantable rods, pellets, plates or fibers, etc.

The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug. Immediate release refers to the release of drug within a short time period following administration, e.g., generally within a few minutes to about 1 to 2 hours.

The term "mammal" refers to organisms from the taxonomy class "mammalian," including but not limited to humans, other primates such as chimpanzees, apes, orangutans and monkeys, rats, mice, cats, dogs, cows, horses, etc. In various embodiments, the mammal is a human patient.

The phrase "release rate profile" refers to the percentage of active ingredient that is released over fixed units of time, e.g., mcg/hr, mcg/day, mg/hr, mg/day, 10% per day for ten days, etc. As persons of ordinary skill know, a release rate profile may be but need not be linear. By way of a non-limiting example, the drug depot may be a pellet that releases at least one analgesic agent in a bolus dose and at least one anti-inflammatory agent over a period of time.

Treating or treatment of a disease or condition refers to executing a protocol, which may include administering one or more drugs to a patient (human, normal or otherwise, or other mammal), in an effort to alleviate signs or symptoms of the disease. Alleviation can occur prior to signs or symptoms of the disease or condition appearing, as well as after their appearance. Thus, "treating" or "treatment" includes "preventing" or "prevention" of disease or undesirable condition. In addition, "treating" or "treatment" does not require complete alleviation of signs or symptoms, does not require a cure, and specifically includes protocols that have only a marginal effect on the patient. "Reducing pain" includes a decrease in pain and does not require complete alleviation of pain signs or symptoms, and does not require a cure. In various embodiments, reducing pain includes even a marginal decrease in pain. By way of example, the administration of the effective dosages of at least one analgesic agent and at least one anti-inflammatory agent may be used to prevent, treat or relieve the symptoms of pain and/or inflammation.

"Localized" delivery includes delivery where one or more drugs are deposited within a tissue, for example, a nerve root of the nervous system or a region of the brain, or in close proximity (within about 10 cm, or preferably within about 5 cm, or within about 1 cm, or less for example) thereto. A "targeted delivery system" provides delivery of one or more drugs depots, gels or depot dispersed in the gel having a quantity of therapeutic agent that can be deposited at or near the target site as needed for treatment of pain, inflammation or other disease or condition.

The term "biodegradable" includes that all or parts of the drug depot will degrade over time by the action of enzymes, by hydrolytic action and/or by other similar mechanisms in the human body. In various embodiments, "biodegradable" includes that the depot (e.g., microparticle, microsphere, etc.) can break down or degrade within the body to non-toxic components after or while a therapeutic agent has been or is being released. By "bioerodible" it is meant that the depot will erode or degrade over time due, at least in part, to contact with substances found in the surrounding tissue, fluids or by cellular action. By "bioabsorbable" it is meant that the depot will be broken down and absorbed within the human body, for example, by a cell or tissue. "Biocompatible" means that the depot will not cause substantial tissue irritation or necrosis at the target tissue site.

The phrase "pain management medication" includes one or more therapeutic agents that are administered to prevent, alleviate or remove pain entirely. These include anti-inflammatory agents, muscle relaxants, analgesics, anesthetics, narcotics, and so forth, and combinations thereof.

In various embodiments, the depot can be designed to cause an initial burst dose of one or more therapeutic agents within the first 24 hours after implantation. "Initial burst" or "burst effect" or "bolus dose" or "pulse dose" refer to the release of therapeutic agent from the depot during the first 24 hours after the depot comes in contact with an aqueous fluid (e.g., synovial fluid, cerebral spinal fluid, etc.). The burst effect may be an immediate release. The "burst effect" is believed to be due to the increased release of therapeutic agent from the depot. The initial burst effect or bolus dose may be determined before hand by formulating the depot by calculating the quotient obtained by dividing (i) the effective amount by weight of therapeutic agent to be released from the depot or region in a predetermined initial period of time after implantation of the depot, by (ii) the total amount of therapeutic agent that is to be delivered from an implanted composition. It is understood that the initial burst may vary depending on the shape and surface area of the implant.

The burst effect with respect to the region or depot, in various embodiments, can be designed so that a larger initial dose may be released over a short period of time to achieve the desired effect. For example, if a drug depot is designed to release 15 mg of morphine per 48 hours, then the initial burst dose or bolus dose region or depot will be designed to release a percentage of the dose within the first 24 hours (e.g., 10 mg of morphine or 66% of the 48 hour dose within 24 hours). Thus, the burst effect of the drug depot or region releases more therapeutic agent than the sustained release region or depot.

A region or depot that utilizes a burst effect or bolus dose will release more therapeutic agent (e.g., analgesic and/or anti-inflammatory) than the sustained release region or depot. For example, particularly with painful chronic conditions including rheumatoid arthritis, osteoarthritis, a spinal disc herniation (e.g., sciatica), carpal/tarsal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, spondilothesis, stenosis, discogenic back pain, and joint pain or the like, the initial burst effect of the drug depot or region of the drug depot will be advantageous as it will provide more immediate pain and/or inflammation relief as a bolus dose of drug will be released at or near the target tissue site and provide the desired reducing, or alleviation of signs or symptoms of pain and/or inflammation. For example, the drug depot or region of the drug depot may release 51%, 52%, 53%, 54%, 55%, % 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% of the daily dose within the first one to twelve hours to reduce, prevent or treat pain and/or inflammation. The pain and/or inflammation may also be due to surgery.

The drug depot comprising at least one analgesic agent or its pharmaceutically acceptable salt and at least one anti-inflammatory agent or its pharmaceutically acceptable salt may be co-administered with a muscle relaxant. Co-administration may involve administering at the same time in separate drug depots or formulating together in the same drug depot.

Exemplary muscle relaxants include by way of example and not limitation, alcuronium chloride, atracurium bescylate, baclofen, carbolonium, carisoprodol, chlorphenesin carbamate, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, or combinations thereof.

The drug depot may also comprise other therapeutic agents or active ingredients in addition to the at least one analgesic agent or its pharmaceutically acceptable salt and at least one anti-inflammatory agent or its pharmaceutically acceptable salt. Suitable additional therapeutic agents include, but are not limited to, integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibodies (daclizumab, basilicimab), ABX (anti IL-8 antibodies), recombinant human IL-10, or HuMax IL-15 (anti-IL 15 antibodies).

Other suitable therapeutic agents that may be co-administered with the anti-inflammatory agent and analgesic agent include IL-1 inhibitors, such Kineret® (anakinra) which is a recombinant, non-glycosylated form of the human inerleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. It is contemplated that where desirable a pegylated form of the above may be used. Examples of other therapeutic agents include NF kappa B inhibitors such as glucocorticoids, antioxidants, such as dilhiocarbamate.

Specific examples of additional therapeutic agents suitable for use include, but are not limited to, an anabolic growth factor or anti-catabolic growth factor, analgesic agent, or an osteoinductive growth factor or a combination thereof.

Suitable anabolic growth or anti-catabolic growth factors include, but are not limited to, a bone morphogenetic protein, a growth differentiation factor, a LIM mineralization protein, CDMP or progenitor cells or a combination thereof.

Suitable analgesic agents include, but are not limited to, acetaminophen, bupivicaine, opioid analgesics such as amitriptyline, carbamazepine, gabapentin, pregabalin, clonidine, opioid analgesics or a combination thereof. Opioid analgesics include, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, tramadol or a combination thereof.

For each of the anti-inflammatory agents and analgesic agents, in some embodiments, the release of each compound may be for at least one, at least two, at least three, at least four, at least five, at least six, at least seven, at least eight, at least nine, at least ten, at least eleven, at least twelve, at least thirteen, at least fourteen, or at least fifteen days, or longer.

Sulfazalazine

In one embodiment, the anti-inflammatory agent comprises sulfasalazine. Sulfasalazine is also known as 6-oxo-3-((4-(pyridin-2-ylsulfamoyl)phenyl)hydrazinylidene]cyclohexa-1,4-diene-1-carboxylic acid. Sulfasalazine or a pharmaceutically acceptable salt thereof is available from various pharmaceutical manufacturers.

In one embodiment, the dosage of sulfasalazine is from approximately 0.005 µg/day to approximately 3000 mg/day. Additional dosages of sulfasalazine include from approximately 0.005 µg/day to approximately 2000 mg/day; approximately 0.005 µg/day to approximately 1000 mg/day; approximately 0.005 µg/day to approximately 100 mg/day; approximately 0.005 µg/day to approximately 1 mg/day; approximately 0.005 µg/day to approximately 80 µg/day; approximately 0.01 µg/day to approximately 70 µg/day; approximately 0.01 µg/day to approximately 65 µg/day; approximately 0.01 µg/day to approximately 60 µg/day; approximately 0.01 µg/day to approximately 55 µg/day; approximately 0.01 µg/day to approximately 50 µg/day; approximately 0.01 µg/day to approximately 45 µg/day; approximately 0.01 to approximately 40 µg/day; approximately 0.025 µg/day to approximately 35 µg/day; approximately 0.025 µg/day to approximately 30 µg/day; approximately 0.025 µg/day to approximately 25 µg/day; approximately 0.025 µg/day to approximately 20 µg/day; and approximately 0.025 µg/day to approximately 15 µg/day. In another embodiment, the dosage of sulfasalazine is from approximately 0.05 µg/day to approximately 15 µg/day. In another embodiment, the dosage of sulfasalazine is from approximately 0.05 to approximately 10 µg/day. The drug depot may release an initial burst dose or bolus dose or pulse dose or immediate release dose based on the daily dosage. The drug depot may release a longer sustained release dose based on the daily dosage.

Sulindac

In one embodiment, the anti-inflammatory agent comprises sulindac. Sulindac, also known as 2-[6-fluoro-2-methyl-3-[(4-methylsulfinylphenyl)-methylidene]inden-1-yl]-acetic acid may be represented by the formula $C_{20}H_{17}FO_3S$. Sulindac or a pharmaceutically acceptable salt thereof is available from various pharmaceutical manufacturers.

The dosage of sulindac may be from approximately 0.001 µg/day to approximately 400 mg/day. Additional dosages of sulindac include from approximately 0.001 µg/day to approximately 200 mg/day; approximately 0.001 µg/day to approximately 100 mg/day; approximately 0.001 µg/day to approximately 1 mg/day; approximately 0.001 to approximately 500 µg/day; approximately 0.001 to approximately 100 µg/day; approximately 0.025 to approximately 75 µg/day; approximately 0.025 to approximately 65 µg/day; approximately 0.025 to approximately 60 µg/day; approximately 0.025 to approximately 55 µg/day; approximately 0.025 to approximately 50 µg/day; approximately 0.025 to approximately 45 µg/day; approximately 0.025 to approximately 40 µg/day; approximately 0.025 to approximately 35 µg/day; approximately 0.005 to approximately 30 µg/day; approximately 0.005 to approximately 25 µg/day; approximately 0.005 to approximately 20 µg/day; and approximately 0.005 to approximately 15 µg/day. In another embodiment, the dosage of sulindac is from approximately 0.01 to approximately 15 µg/day. In another embodiment, the dosage of sulindac is from approximately 0.01 to approximately 10 µg/day. In another embodiment, the dosage of sulindac is from approximately 0.01 to approximately 5 µg/day. In another embodiment, the dosage of sulindac is from approximately 0.01 to approximately 20 µg/day. In another embodiment, the sulindac is administered in a drug depot that releases 9.6 µg/day. The drug depot may release an initial burst dose or bolus dose or pulse dose or immediate release dose based on the daily dosage. The drug depot may release a longer sustained release dose based on the daily dosage.

Clonidine

In one embodiment, the anti-inflammatory agent is clonidine, also referred to as 2,6-dichloro-N-2-imidazolidinyldenebenzenamine. Clonidine or a pharmaceutically acceptable salt thereof is available from various pharmaceutical manufactures. In various embodiments, the clonidine may be in free acid form or the HCL.

The dosage may be from approximately 0.0005 to approximately 100 µg/kg/day. Additional dosages of clonidine include from approximately 0.0005 to approximately 95 µg/kg/day; approximately 0.0005 to approximately 90 µg/kg/day; approximately 0.0005 to approximately 85 µg/kg/day; approximately 0.0005 to approximately 80 µg/kg/day; approximately 0.0005 to approximately 75 µg/kg/day; approximately 0.001 to approximately 70 µg/kg/day; approximately 0.001 to approximately 65 µg/kg/day; approximately 0.001 to approximately 60 µg/kg/day; approximately 0.001 to approximately 55 µg/kg/day; approximately 0.001 to approximately 50 µg/kg/day; approximately 0.001 to approximately 45 µg/kg/day; approximately 0.001 to approximately 40 µg/kg/day; approximately 0.001 to approximately 35 µg/kg/day; approximately 0.0025 to approximately 30 µg/kg/day; approximately 0.0025 to approximately 25 µg/kg/day; approximately 0.0025 to approximately 20 µg/kg/day; and approximately 0.0025 to approximately 15 µg/kg/day. In another embodiment, the dosage of clonidine is from approximately 0.005 to approximately 15 µg/kg/day. In another embodiment, the dosage of clonidine is from approximately 0.005 to approximately 10 µg/kg/day. In another embodiment, the dosage of clonidine is from approximately 0.005 to approximately 5 µg/kg/day. In another embodiment, the dosage of clonidine is from approximately 0.005 to 2.5µ/kg/day. In some embodiments, the amount of clonidine is between 40 and 600 µg/day. In some embodiments, the amount of clonidine is between 200 and 400 µg/day. The drug depot may release an initial burst dose or bolus dose or pulse dose or immediate release dose based on the daily dosage. The drug depot may release a longer sustained release dose based on the daily dosage.

Fluocinolone

In one embodiment, the anti-inflammatory agent comprises fluocinolone acetonide. Fluocinolone is available from various pharmaceutical manufacturers.

Fluocinolone is available from various pharmaceutical manufacturers. The dosage of fluocinolone may be from approximately 0.0005 to approximately 100 µg/day. Additional dosages of fluocinolone include from approximately 0.0005 to approximately 50 µg/day; approximately 0.0005 to approximately 25 µg/day; approximately 0.0005 to approximately 10 µg/day; approximately 0.0005 to approximately 5 µg/day; approximately 0.0005 to approximately 1 µg/day; approximately 0.005 to approximately 0.75 µg/day; approximately 0.0005 to approximately 0.5 µg/day; approximately 0.0005 to approximately 0.25 µg/day; approximately 0.0005 to approximately 0.1 µg/day; approximately 0.0005 to approximately 0.075 µg/day; approximately 0.0005 to approximately 0.05 µg/day; approximately 0.001 to approximately 0.025 µg/day; approximately 0.001 to approximately 0.01 µg/day; approximately 0.001 to approximately 0.0075 µg/day; approximately 0.001 to approximately 0.005 µg/day; approximately 0.001 to approximately 0.025 µg/day; and 0.002 to approximately 0.025 µg/day. In another embodiment, the dosage of fluocinolone is from approximately 0.001 to approximately 15 µg/day. In another embodiment, the dosage of fluocinolone is from approximately 0.001 to approximately 10 µg/day. In another embodiment, the dosage of fluocinolone is from approximately 0.001 to approximately 5 µg/day. In another embodiment, the dosage of fluocinolone is from approximately 0.001 to 2.5 µg/day. In some embodiments, the amount of fluocinolone is between 40 and 600 µg/day. In some embodiments, the amount of fluocinolone is between 200 and 400 µg/day. Dosing formulations may be prepared to contain a sufficient amount of the active ingredient to enable the desired about of compound to be release over the desired amount of time.

In some embodiments, there is sufficient fluocinolone such that the fluocinolone is released at a rate of 2-3 µg per day for a period of at least three days. In some embodiments, this release rate continues for, at least ten days, at least fifteen days, at least twenty-five days, at least thirty days, at least fifty days, at least ninety days, at least one hundred days, at least one-hundred and thirty-five days, at least one-hundred and fifty days, or at least one hundred and eighty days. The drug depot may release an initial burst dose or bolus dose or pulse dose or immediate release dose based on the daily dosage. The drug depot may release a longer sustained release dose based on the daily dosage.

Dexamethasone

In one embodiment of the present invention, the anti-inflammatory agent is dexamethasone, also referred to as 8S,9R,10S,11S,13S,14S,16R,17R)-9-Fluoro-11,17-dihydroxy-17-(2-hydroxyacetyl)-10,13,16-trimethyl-6,7,8,11, 12,14,15,16 octahydrocyclopenta[a]-phenanthren-3-one), or a pharmaceutically acceptable salt thereof, which is available from various manufacturers.

In various embodiments, dexamethasone may be released from the depot at a dose of about 10 pg to about 80 mg/day, about 2.4 ng/day to about 50 mg/day, about 50 ng/day to about 2.5 mg/day, about 250 ng/day to about 250 ug/day, about 250 ng/day to about 50 ug/day, about 250 ng/day to about 25 ug/day, about 250 ng/day to about 1 ug/day, about 300 ng/day to about 750 ng/day or about 0.50 ug/day. In various embodiments, the dose may be about 0.01 to about 10 µg/day or about 1 ng to about 120 µg/day. The drug depot may release an initial burst dose or bolus dose or pulse dose or immediate release dose based on the daily dosage. The drug depot may release a longer sustained release dose based on the daily dosage.

In one exemplary embodiment, the dexamethasone is dexamethasone acetate, or sodium phosphate.

Lovastatin

In one exemplary embodiment, the anti-inflammatory agent comprises lovastatin. Lovastatin is a statin that may be obtained from various manufacturers in various forms (e.g., injection, powder, etc.). For example, lovastatin may be obtained from Merck as Mevacor® (see U.S. Pat. No. 4,231, 938, the entire disclosure is herein incorporated by reference). Suitable pharmaceutically acceptable salts of lovastatin include one or more compounds derived from bases such as sodium hydroxide, potassium hydroxide, lithium hydroxide, calcium hydroxide, 1-deoxy-2-(methylamino)-D-glucitol, magnesium hydroxide, zinc hydroxide, aluminum hydroxide, ferrous or ferric hydroxide, ammonium hydroxide or organic amines such as N-methylglucamine, choline, arginine or the like or combinations thereof. Suitable pharmaceutically acceptable salts of lovastatin include lithium, calcium, hemicalcium, sodium, potassium, magnesium, aluminum, ferrous or ferric salts thereof or a combination thereof.

In various embodiments, the therapeutically effective amount of lovastatin comprises from about 0.1 pg to about 2000 mg, for example, 0.1 ng to 1000 mg, 500 mg, 100 mg, 50 mg, 25 mg, 10 mg, 1 mg, 50 µg, 25 µg, 10 µg, 1 µg, 500 ng, 250 ng, 100 ng, 75 ng, 50 ng, 25 ng, 15 ng, 10 ng, 5 ng, or 1 ng of lovastatin per day. In various embodiments, the dosage may be, for example from about 3 ng/day to 0.3 µg/day. The drug depot may release an initial burst dose or bolus dose or pulse dose or immediate release dose based on the daily dosage. The drug depot may release a longer sustained release dose based on the daily dosage.

Morphine

In one embodiment of the present invention, the analgesic agent is morphine. Morphine is also referred to as (5α,6α)-7,8-didehydro-4,5-epoxy-17-methylmorphinan-3,6-diol and has the chemical formula $C_{17}H_{19}NO_3$. Morphine and a pharmaceutically acceptable salt thereof is available from various manufacturers. In one exemplary embodiment, the morphine comprises morphine sulfate or hydrochloride.

The dosage of the morphine may be from 0.1 mg to 1000 mg per day. For example, the dosage of morphine may be for example, 0.1 mg to 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 75 mg, 80 mg, 85 mg, 90 mg, 95 mg, 100 mg, 120 mg, 130 mg, 140 mg, 150 mg, 160 mg, 170 mg, 180 mg, 190 mg, 200 mg of morphine per day. The drug depot may release an initial burst dose or bolus dose or pulse dose or immediate release dose based on the daily dosage. The drug depot may release a longer sustained release dose based on the daily dosage.

Tramadol

In one embodiment, the analgesic agent is tramadol. Tramadol is also referred to as (±)cis-2-[(dimethylamino)methyl]-1-(3-methoxyphenyl)cyclohexanol hydrochloride and has the chemical formula $C_{16}H_{25}NO_2$. Tramadol or a pharmaceutically acceptable salt thereof is available from various manufacturers. In one embodiment, the tramadol comprises tramadol HCL.

The dosage of the tramadol may be from 0.01 mg to 500 mg per day. For example, the dosage of tramadol may be for example, 0.1 mg to 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 75 mg, 80 mg, 85 mg, 90 mg, 95 mg, 100 mg, 120 mg, 130 mg, 140 mg, 150 mg, 160 mg, 170 mg, 180 mg, 190 mg, 200 mg, or 500 mg of tramadol per day.

In one embodiment, the drug depot contains sufficient tramadol to release between 2.5 and 30 mg/kg/day. In another embodiment the drug depot contains sufficient tramadol to release between 3 and 27.5 mg/kg/day. The drug depot may release an initial burst dose or bolus dose or pulse dose or immediate release dose based on the daily dosage. The drug depot may release a longer sustained release dose based on the daily dosage.

The at least one anti-inflammatory agent and at least one analgesic agent may also be administered with non-active ingredients. These non-active ingredients may have multi-functional purposes including the carrying, stabilizing and controlling the release of the therapeutic agent(s). The sustained release process, for example, may be by a solution-diffusion mechanism or it may be governed by an erosion-sustained process. Typically, the depot will be a solid or semi-solid formulation comprised of a biocompatible material that can be biodegradable. The term "solid" is intended to mean a rigid material, while "semi-solid" is intended to mean a material that has some degree of flexibility, thereby allowing the depot to bend and conform to the surrounding tissue requirements.

In various embodiments, the non-active ingredients will be durable within the tissue site for a period of time equal to (for biodegradable components) or greater than (for non-biodegradable components) the planned period of drug delivery. For example, the depot material may have a melting point or glass transition temperature close to or higher than body temperature, but lower than the decomposition or degradation temperature of the therapeutic agent. However, the pre-determined erosion of the depot material can also be used to provide for slow release of the loaded therapeutic agent(s).

In various embodiments, the drug depot may not be biodegradable or comprise material that is not biodegradable. Non-biodegradable polymers include, but are not limited to, various cellulose derivatives (carboxymethyl cellulose, cellulose acetate, cellulose acetate propionate, ethyl cellulose, hydroxypropyl methyl cellulose, hydroxyalkyl methyl celluloses, and alkyl celluloses), silicon and silicon-based polymers (such as polydimethylsiloxane), polyethylene-co-(vinyl acetate), poloxamer, polyvinylpyrrolidone, poloxamine, polypropylene, polyamide, polyacetal, polyester, poly ethylene-chlorotrifluoroethylene, polytetrafluoroethylene (PTFE or "Teflon™"), styrene butadiene rubber, polyethylene, polypropylene, polyphenylene oxide-polystyrene, poly-α-chloro-p-xylene, polymethylpentene, polysulfone, non-degradable ethylene-vinyl acetate (e.g., ethylene vinyl acetate disks and poly(ethylene-co-vinyl acetate)), and other related biostable polymers or combinations thereof.

The drug depot may comprise non-resorbable polymers as well. These non-resorbable polymers can include, but are not limited to, delrin, polyurethane, copolymers of silicone and polyurethane, polyolefins (such as polyisobutylene and polyisoprene), acrylamides (such as polyacrylic acid and poly(acrylonitrile-acrylic acid)), neoprene, nitrile, acrylates (such as polyacrylates, poly(2-hydroxy ethyl methacrylate), methyl methacrylate, 2-hydroxyethyl methacrylate, and copolymers of acrylates with N-vinyl pyrrolidone), N-vinyl lactams, polyacrylonitrile, glucomannan gel, vulcanized rubber and combinations thereof. Examples of polyurethanes include thermoplastic polyurethanes, aliphatic polyurethanes, segmented polyurethanes, hydrophilic polyurethanes, polyether-urethane, polycarbonate-urethane and silicone polyether-urethane. Typically, the non-degradable drug depots may need to be removed.

In some instance, it may be desirable to avoid having to remove the drug depot after use. In those instances, the depot may comprise a biodegradable material. There are numerous materials available for this purpose and having the characteristic of being able to breakdown or disintegrate over a prolonged period of time when positioned at or near the target tissue. As a function of the chemistry of the biodegradable material, the mechanism of the degradation process can be hydrolytical or enzymatical in nature, or both. In various embodiments, the degradation can occur either at the surface (heterogeneous or surface erosion) or uniformly throughout the drug delivery system depot (homogeneous or bulk erosion).

In various embodiments, the depot may comprise a bioabsorbable, and/or a biodegradable biopolymer that may provide immediate release, or sustained release of the at least one analgesic agent and at least one anti-inflammatory agent. Examples of suitable sustained release biopolymers include but are not limited to poly (alpha-hydroxy acids), poly (lactide-co-glycolide) (PLGA or PLG), polylactide (PLA), polyglycolide (PG), polyethylene glycol (PEG) conjugates of poly (alpha-hydroxy acids), polyorthoesters, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, poly(glycolide-,-caprolactone), ,-caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. As persons of ordinary skill are aware, mPEG may be used as a plasticizer for PLGA, but other polymers/excipients may be used to achieve the same effect. mPEG imparts malleability to the resulting formulations.

Where different combinations of polymers are used (bi, tri (e.g., PLGA-PEO-PLGA) or terpolymers), they may be used in different molar ratios, 1:1, 2:1, 3:1, 4:1, 5:1, 6:1, 7:1, 8:1, 9:1, or 10:1. For example, for a 130-day release drug depot, the polymer make up is 50:50 PLGA to 100 PLA. The molecular weight range is 0.45 to 0.8 dI/g.

In various embodiments, the molecular weight of the polymer can be a wide range of values. The average molecular weight of the polymer can be from about 1000 to about 10,000,000; or about 1,000 to about 1,000,000; or about 5,000 to about 500,000; or about 10,000 to about 100,000; or about 20,000 to 50,000.

In some embodiments, the at least one biodegradable polymer comprises poly(lactic-co-glycolic acid) (PLA) or poly(orthoester) (POE) or a combination thereof. The poly(lactic-co-glycolic acid) may comprise a mixture of polyglycolide (PGA) and polylactide and in some embodiments, in the mixture, there is more polylactide than polyglycolide. In various other embodiments there is 100% polylactide and 0% polyglycolide; 95% polylactide and 5% polyglycolide; 90% polylactide and 10% polyglycolide; 85% polylactide and 15% polyglycolide; 80% polylactide and 20% polyglycolide; 75% polylactide and 25% polyglycolide; 70% polylactide and 30% polyglycolide; 65% polylactide and 35% polyglycolide; 60% polylactide and 40% polyglycolide; 55% polylactide and 45% polyglycolide; 50% polylactide and 50% polyglycolide; 45% polylactide and 55% polyglycolide; 40% polylactide and 60% polyglycolide; 35% polylactide and 65% polyglycolide; 30% polylactide and 70% polyglycolide; 25% polylactide and 75% polyglycolide; 20% polylactide and 80% polyglycolide; 15% polylactide and 85% polyglycolide; 10% polylactide and 90% polyglycolide; 5% polylactide and 95% polyglycolide; and 0% polylactide and 100% polyglycolide.

In various embodiments that comprise both polylactide and polyglycolide; there is at least 95% polylactide; at least 90% polylactide; at least 85% polylactide; at least 80% polylactide; at least 75% polylactide; at least 70% polylactide; at least 65% polylactide; at least 60% polylactide; at least 55%; at least 50% polylactide; at least 45% polylactide; at least 40% polylactide; at least 35% polylactide; at least 30% polylactide; at least 25% polylactide; at least 20% polylactide; at least 15% polylactide; at least 10% polylactide; or at least 5% polylactide; and the remainder of the biopolymer being polyglycolide.

In some embodiments, the biodegradable polymer comprises at least 10 wt %, at least 50 wt. %, at least 60 wt. %, at least 70 wt. %, at least 80 wt. %, at least 85 wt. %, at least 90 wt. %, at least 95 wt. %, or at least 99 wt. % of the formulation. In some embodiments, the at least one biodegradable polymer and the analgesic and the anti-inflammatory are the only components of the pharmaceutical formulation.

In some embodiments, at least 75% of the particles have a size from about 1 micrometer to about 250 micrometers. In some embodiments, at least 85% of the particles have a size from about 1 micrometer to about 100 micrometers. In some embodiments, at least 95% of the particles have a size from about 1 micrometer to about 30 micrometers. In some embodiments, all of the particles have a size from about 1 micrometer to about 30 micrometers.

In some embodiments, at least 75% of the particles have a size from about 5 micrometer to about 20 micrometers. In some embodiments, at least 85% of the particles have a size from about 5 micrometers to about 20 micrometers. In some embodiments, at least 95% of the particles have a size from about 5 micrometer to about 20 micrometers. In some embodiments, all of the particles have a size from about 5 micrometer to about 250 micrometers.

The depot may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfite, sodium bisulfate, sodium thiosulfate, thimerosal, methylparaben, polyvinyl alcohol and phenylethyl alcohol; solubility adjusting agents; stabilizers; and/or cohesion modifiers. Typically, any such inactive materials will be present within the range of 0-75 wt %, and more typically within the range of 0-30 wt %. If the depot is to be placed in the spinal area, in various embodiments, the depot may comprise sterile preservative free material.

The depot can be different sizes, shapes and configurations. There are several factors that can be taken into consideration in determining the size, shape and configuration of the drug depot. For example, both the size and shape may allow for ease in positioning the drug depot at the target tissue site that is selected as the implantation or injection site. In addition, the shape and size of the system should be selected so as to minimize or prevent the drug depot from moving after implantation or injection. In various embodiments, the drug depot can be shaped like a pellet, a sphere, a cylinder such as a rod or fiber, a flat surface such as a disc, film or sheet, or the like. Flexibility may be a consideration so as to facilitate placement of the drug depot. In various embodiments, the drug depot can be different sizes, for example, the drug depot may be a length of from about 0.5 mm to 5 mm and have a diameter of from about 0.01 to about 2 mm. In various embodiments, the drug depot may have a layer thickness of from about 0.005 to 1.0 mm, such as, for example, from 0.05 to 0.75 mm.

Radiographic markers can be included on the drug depot to permit the user to position the depot accurately into the target site of the patient. These radiographic markers will also permit the user to track movement and degradation of the depot at the site over time. In this embodiment, the user may accurately position the depot in the site using any of the numerous diagnostic imaging procedures. Such diagnostic imaging procedures include, for example, X-ray imaging or fluoroscopy. Examples of such radiographic markers include, but are not limited to, barium, calcium phosphate, and/or metal beads or particles. In various embodiments, the radiographic marker could be a spherical shape or a ring around the depot.

FIG. 1 is a schematic drawing illustrating an embodiment of one drug depot 10 composition having a first region or layer 12 capable of releasing a therapeutically effective burst amount or bolus dose or pulse dose or immediate release of the analgesic and/or the anti-inflammatory agent as the depot comes in contact with the bodily fluid and the layer or region degrades and releases the therapeutic agent(s). In this way, short-term relief of pain and/or inflammation can be provided to the patient. A second layer or region (shown as the core) of the depot shown as 14 is capable of releasing a therapeutically effective amount of the analgesic and the anti-inflammatory agent over a longer period of time (e.g, at least 3 days to 6 months) as this region or layer comes into contact with bodily fluid.

Although the initial burst region or layer is shown separately from the sustained release layer, it will be understood that the initial burst region or layer may be combined with the sustained release region or layer and thus when fluid contacts the depot each layer will release at different release rates. It will also be understood that, although the depot is shown with two layers or regions (12 and 14), the depot may comprise one or multiple layers or regions (e.g., two, three, four, five, six, seven, eight, nine ten, etc.). For example, a first immediate release layer or region may be disposed on a first sustained release layer and a second immediate release layer may be disposed on the first sustained release layer, and so on. It will also be understood that the depot may be formed from a mixture of a sustained release formulation with a burst release formulation that are combined together.

For example, the depot may be formed from separate different micelles (one or more bolus release micelle and one or more sustained release micelles) having different release profiles that are combined together. In various embodiments, the plurality of depots may comprise biodegradable therapeutic particles dispersed within a gel and as the gel degrades, the therapeutic particles are released.

FIG. 1A is a schematic drawing illustrating an embodiment of one drug depot composition 10 having a plurality of regions 12 capable of releasing a therapeutically effective burst amount or bolus dose or pulse dose or immediate release of the analgesic and/or the anti-inflammatory agent as the region degrades when it comes into contact with bodily fluid. Region 14 is capable of releasing a therapeutically effective amount of the analgesic and the anti-inflammatory agent over a longer period of time (sustained release over a longer period of time) as the region degrades when it comes into contact with bodily fluid.

Figure 2:
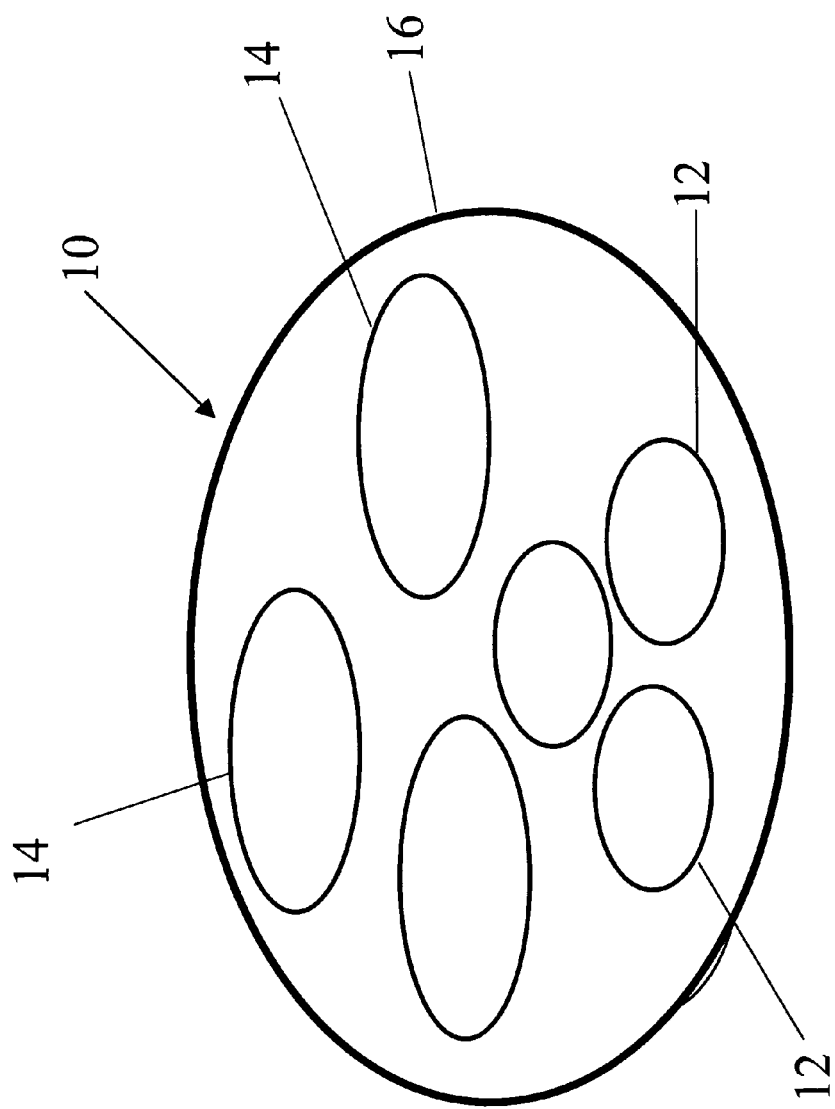
FIG. 2 is a schematic drawing illustrating an embodiment of one drug depot composition having a plurality of regions capable of releasing a therapeutically effective bolus amount of the analgesic and/or the anti-inflammatory agent and a plurality of regions capable of releasing a therapeutically effective amount of the analgesic and/or the anti-inflammatory agent over a longer period of time.

FIG. 2 is a schematic drawing illustrating an embodiment of one drug depot composition having a plurality of regions 12 capable of releasing a therapeutically effective a burst amount or bolus dose or pulse dose or immediate release of the analgesic and/or the anti-inflammatory agent, when bodily fluids come in contact with the region. A plurality of regions 14 are provided and are capable of releasing a therapeutically effective amount of the analgesic and the anti-inflammatory agent over a longer period of time, when bodily fluid come in contact with these regions. The regions 12 and 14 may be housed in the drug depot housing 16, which also may be biodegradable as well as the regions.

Figure 3:
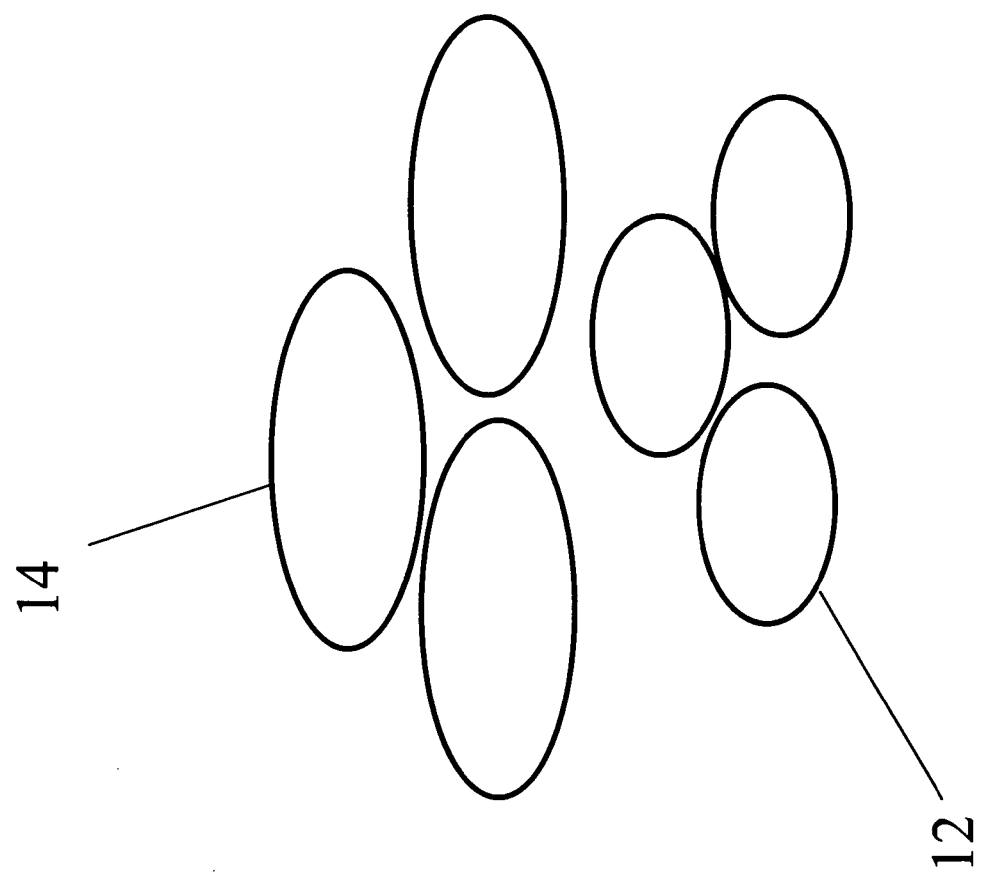
FIG. 3 is a schematic drawing illustrating an embodiment of a plurality of drug depots, a first set of drug depots capable of releasing a therapeutically effective bolus amount of the analgesic and/or the anti-inflammatory agent and a second set of drug depots capable of releasing a therapeutically effective amount of the analgesic and/or the anti-inflammatory agent over a longer period of time.

FIG. 3 is a schematic drawing illustrating an embodiment of a plurality of drug depots, a first set of drug depots 12 capable of releasing a therapeutically effective burst amount or bolus dose or pulse dose or immediate release of the analgesic and/or the anti-inflammatory agent and a plurality of regions 14 capable of releasing a therapeutically effective amount of the analgesic and the anti-inflammatory agent over a longer period of time (sustained release). Thus, in this embodiment, there is a set of drug depots. One set may have a burst release or bolus release or pulse release or immediate release and the other set may be sustained release over a longer period of time. Thus, the first and second depot set have different release profiles. In this embodiment, a number of pellets for different diseases/conditions (e.g., sciatica, post-operative pain etc.) with various drug release kinetics, some with fast release and other with slow release can be implanted together thus avoiding the need for one drug depot with complicated release kinetics. In conditions, for example, post-operative pain, one can implant 3-5 strips at the surgical site in one patient at a time to reduce, prevent or treat post-operative pain.

A strategy of triangulation may be effective when administering these multiple depot pharmaceutical formulations. Thus, a plurality (at least two, at least three, at least four, at least five, at least six, at least seven, etc.) drug depots comprising the pharmaceutical formulations may be placed around the target tissue site (also known as the pain generator or pain generation site) such that the target tissue site falls within a region that is either between the formulations when there are two, or within an area whose perimeter is defined by a set of plurality of formulations.

Various factors can be adjusted to achieve the initial burst of therapeutic agent release. First, the initial burst can be controlled by factors related to the property of the depot, such as the water immiscibility of the solvent, polymer/solvent ratio, and the property of the polymer. The extent of water immiscibility of the solvent used in the depot affects that rate aqueous body fluid can penetrate the depot to release the therapeutic agent. Generally, higher water solubility leads to a higher initial burst while water immiscibility leads to a lower initial burst or slower release (sustained release) of the therapeutic agent.

Suitable solvents that can be used to control initial burst release or sustained release include, but are not limited to, methyl benzoate, ethyl benzoate, n-propyl benzoate, isopropyl benzoate, butyl benzoate, isobutyl benzoate, sec-butyl benzoate, tert-butyl benzoate, isoamyl benzoate, benzyl benzoate, water, alcohol, low molecular weight PEG (less than 1,000 MW), triacetin, diacetin, tributyrin, triethyl citrate, tributyl citrate, acetyl triethyl citrate, acetyl tributyl citrate, triethylglycerides, triethyl phosphate, diethyl phthalate, diethyl tartrate, mineral oil, polybutene, silicone fluid, glycerin, ethylene glycol, octanol, ethyl lactate, propylene glycol, propylene carbonate, ethylene carbonate, butyrolactone, ethylene oxide, propylene oxide, N-methyl-2-pyrrolidone, 2-pyrrolidone, glycerol formal, methyl acetate, ethyl acetate, methyl ethyl ketone, dimethylformamide, glycofurol, dimethyl sulfoxide, tetrahydrofuran, caprolactam, decylmethylsulfoxide, oleic acid, 1-dodecylazacyclo-heptan-2-one, or mixtures thereof. The solvent can be mixed, in various embodiments, with the therapeutic agent and/or polymers to obtain the desired release profile.

The depot may have pore forming agents, which include biocompatible materials that when contacted with body fluids dissolve, disperse or degrade to create pores or channels in the polymer matrix. Typically, organic and non-organic materials that are water soluble such as sugars (e.g., sucrose, dextrose), water soluble salts (e.g., sodium chloride, sodium phosphate, potassium chloride, and sodium carbonate), water soluble solvents such as N-methyl-2-pyrrolidone and polyethylene glycol and water soluble polymers (e.g., carboxymethylcellulose, hydroxypropyl-cellulose, and the like) can conveniently be used as pore formers. Such materials may be present in amounts varying from about 0.1% to about 100% of the weight of the polymer, but will typically be less than 50% and more typically less than 10-20% of the weight of polymer.

Further, varying the molecular weight of the polymer in the depot, or adjusting the molecular weight distribution of the polymer material in the depot vehicle can affect the initial burst and the release rate of therapeutic agent from the depot. Generally, a higher molecular weight polymer renders a lower initial burst and slower release rate of the therapeutic agent. The polymers may have different end groups such as acid and ester end groups. As persons of ordinary skill in the art are aware, implantable elastomeric depot compositions having a blend of polymers with different end groups are used the resulting formulation will have a lower burst index and a regulated duration of delivery. For example, one may use polymers with acid (e.g., carboxylic acid) and ester end groups (e.g., methyl of ethyl ester end groups).

Additionally, by varying the comonomer ratio of the various monomers that form a polymer (e.g., the L/G (lactic acid/glycolic acid) or G/CL (glycolic acid/polycaprolactone) ratio for a given polymer) there will be a resulting depot composition having a regulated burst index and duration of delivery. For example, a depot composition having a polymer with a L/G ratio of 50:50 may have a short duration of delivery ranging from about two days to about one month; a depot composition having a polymer with a L/G ratio of 65:35 may have a duration of delivery of about two months; a depot composition having a polymer with a L/G ratio of 75:25 or L/CL ratio of 75:25 may have a duration of delivery of about three months to about four months; a depot composition having a polymer ratio with a L/G ratio of 85:15 may have a duration of delivery of about five months; a depot composition having a polymer with a L/CL ratio of 25:75 or PLA may have a duration of delivery greater than or equal to six months; a depot composition having a terpolymer of CL/G/L with G greater than 50% and L greater than 10% may have a duration of delivery of about one month and a depot composition having a terpolymer of CL/G/L with G less than 50% and L less than 10% may have a duration months up to six months. In general, increasing the G content relative to the CL content shortens the duration of delivery whereas increasing the CL content relative to the G content lengthens the duration of delivery. Thus, among other things, depot compositions having a blend of polymers having different molecular weights, end groups and comonomer ratios can be used to create a depot formulation having a lower burst index and a regulated duration of delivery.

Factors such as the particle size, the disintegration of the particulates, the morphology of the particulates (e.g., whether pores are present in the particulates before implanting or can be formed easily by body fluid attack), coatings, complex formation by the therapeutic agent and the strength of complex bond, can be manipulated to achieve the desired low initial burst and release rate.

In various embodiments, the drug depot comprises poly (lactide-co-glycolide) (PLGA), polylactide (PLA), polyglycolide (PGA), D-lactide, D,L-lactide, L-lactide, D,L-lactide-ε-caprolactone, D,L-lactide-glycolide-ε-caprolactone, glycolide-caprolactone or a combination thereof.

Gel

In various embodiments, the gel has a pre-dosed viscosity in the range of about 1 to about 500 centipoise (cps), 1 to about 200 cps, or 1 to about 100 cps. After the gel is administered to the target site, the viscosity of the gel will increase and the gel will have a modulus of elasticity (Young's modulus) in the range of about $1 \times 10^4$ to about $6 \times 10^5$ dynes/cm$^2$, or $2 \times 10^4$ to about $5 \times 10^5$ dynes/cm$^2$, or $5 \times 10^4$ to about $5 \times 10^5$ dynes/cm$^2$.

In one embodiment, a depot comprises an adherent gel comprising at least one analgesic agent and at least one anti-inflammatory agent that is evenly distributed throughout the gel. The gel may be of any suitable type, as previously indicated, and should be sufficiently viscous so as to prevent the gel from migrating from the targeted delivery site once deployed; the gel should, in effect, "stick" or adhere to the targeted tissue site. The gel may, for example, solidify upon contact with the targeted tissue or after deployment from a targeted delivery system. The targeted delivery system may be, for example, a syringe, a catheter, needle or cannula or any other suitable device. The targeted delivery system may inject the gel into or on the targeted tissue site. The therapeutic agent may be mixed into the gel prior to the gel being deployed at the targeted tissue site. In various embodiments, the gel may be part of a two-component delivery system and when the two components are mixed, a chemical process is activated to form the gel and cause it to stick or to adhere to the target tissue.

In various embodiments, a gel is provided that hardens or stiffens after delivery. Typically, hardening gel formulations may have a pre-dosed modulus of elasticity in the range of about $1 \times 10^4$ to about $3 \times 10^5$ dynes/cm$^2$, or $2 \times 10^4$ to about $2 \times 10^5$ dynes/cm$^2$, or $5 \times 10^4$ to about $1 \times 10^5$ dynes/cm$^2$. The post-dosed hardening gels (after delivery) may have a rubbery consistency and have a modulus of elasticity in the range of about $1 \times 10^4$ to about $2 \times 10^6$ dynes/cm$^2$, or $1 \times 10^5$ to about $7 \times 10^5$ dynes/cm$^2$, or $2 \times 10^5$ to about $5 \times 10^5$ dynes/cm$^2$.

In various embodiments, for those gel formulations that contain a polymer, the polymer concentration may affect the rate at which the gel hardens (e.g., a gel with a higher concentration of polymer may coagulate more quickly than gels having a lower concentration of polymer). In various embodiments, when the gel hardens, the resulting matrix is solid but is also able to conform to the irregular surface of the tissue (e.g., recesses and/or projections in bone).

The percentage of polymer present in the gel may also affect the viscosity of the polymeric composition. For example, a composition having a higher percentage by weight of polymer is typically thicker and more viscous than a composition having a lower percentage by weight of polymer. A more viscous composition tends to flow more slowly. Therefore, a composition having a lower viscosity may be preferred in some instances.

In various embodiments, the molecular weight of the gel can be varied by any one of the many methods known in the art. The choice of method to vary molecular weight is typically determined by the composition of the gel (e.g., polymer versus non-polymer). For example in various embodiments, when the gel comprises one or more polymers, the degree of polymerization can be controlled by varying the amount of polymer initiators (e.g. benzoyl peroxide), organic solvents or activator (e.g. DMPT), crosslinking agents, polymerization agent, and/or reaction time.

Suitable gel polymers may be soluble in an organic solvent. The solubility of a polymer in a solvent varies depending on the crystallinity, hydrophobicity, hydrogen-bonding and molecular weight of the polymer. Lower molecular weight polymers will normally dissolve more readily in an organic solvent than high-molecular weight polymers. A polymeric gel, which includes a high molecular weight polymer, tends to coagulate or solidify more quickly than a polymeric composition, which includes a low-molecular weight polymer. Polymeric gel formulations, which include high molecular weight polymers, also tend to have a higher solution viscosity than a polymeric gel, which include a low-molecular weight polymer.

When the gel is designed to be a flowable gel, it can vary from low viscosity, similar to that of water, to a high viscosity, similar to that of a paste, depending on the molecular weight and concentration of the polymer used in the gel. The viscosity of the gel can be varied such that the polymeric composition can be applied to a patient's tissues by any convenient technique, for example, by brushing, dripping, injecting, or painting. Different viscosities of the gel will depend on the technique used to apply the composition.

In various embodiments, the gel has an inherent viscosity (abbreviated as "I.V." and units are in deciliters/gram), which is a measure of the gel's molecular weight and degradation time (e.g., a gel with a high inherent viscosity has a higher molecular weight and longer degradation time). Typically, a gel with a high molecular weight provides a stronger matrix and the matrix takes more time to degrade. In contrast, a gel with a low molecular weight degrades more quickly and provides a softer matrix. In various embodiments, the gel has a molecular weight, as shown by the inherent viscosity, from about 0.10 dL/g to about 1.2 dL/g or from about 0.10 dL/g to about 0.40 dL/g.

In various embodiments, the gel can have a viscosity of about 300 to about 5,000 centipoise (cp). In other embodiments, the gel can have a viscosity of from about 5 to about 300 cps, from about 10 cps to about 50 cps, from about 15 cps to about 75 cps at room temperature. The gel may optionally have a viscosity enhancing agent such as, for example, hydroxypropyl cellulose, hydroxypropyl methylcellulose, hydroxyethyl methylcellulose, carboxymethylcellulose and salts thereof, Carbopol, poly-(hydroxyethylmethacrylate), poly-(methoxyethylmethacrylate), poly(methoxyethoxyethyl methacrylate), polymethylmethacrylate (PMMA), methylmethacrylate (MMA), gelatin, polyvinyl alcohols, propylene glycol, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

In various embodiments, when a polymer is employed in the gel, the polymeric composition includes about 10 wt % to about 90 wt % or about 30 wt % to about 60 wt % of the polymer.

In various embodiments, the gel is a hydrogel made of high molecular weight biocompatible elastomeric polymers of synthetic or natural origin. A desirable property for the hydrogel to have is the ability to respond rapidly to mechanical stresses, particularly shears and loads, in the human body.

Hydrogels obtained from natural sources are particularly appealing because they are more likely to be biodegradable and biocompatible for in vivo applications. Suitable hydrogels include natural hydrogels, such as, for example, gelatin, collagen, silk, elastin, fibrin and polysaccharide-derived polymers like agarose, and chitosan, glucomannan gel, hyaluronic acid, polysaccharides, such as cross-linked carboxyl-containing polysaccharides, or a combination thereof. Synthetic hydrogels include, but are not limited to those formed from polyvinyl alcohol, acrylamides such as polyacrylic acid and poly (acrylonitrile-acrylic acid), polyurethanes, polyethylene glycol (e.g., PEG 3350, PEG 4500, PEG 8000), silicone, polyolefins such as polyisobutylene and polyisoprene, copolymers of silicone and polyurethane, neoprene, nitrile, vulcanized rubber, poly(N-vinyl-2-pyrrolidone), acrylates such as poly(2-hydroxy ethyl methacrylate) and copolymers of acrylates with N-vinyl pyrolidone, N-vinyl lactams, polyacrylonitrile or combinations thereof. The hydrogel materials may further be cross-linked to provide further strength as needed. Examples of different types of polyurethanes include thermoplastic or thermoset polyurethanes, aliphatic or aromatic polyurethanes, polyetherurethane, polycarbonate-urethane or silicone polyether-urethane, or a combination thereof.

In various embodiments, rather than directly admixing the therapeutic agents into the gel, microspheres may be dispersed within the gel, the microspheres being loaded with at least one analgesic agent and at least one anti-inflammatory agent. In one embodiment, the microspheres provide for a sustained release of the at least one analgesic agent and at least one anti-inflammatory agent. In yet another embodiment, the gel, which is biodegradable, prevents the microspheres from releasing the at least one analgesic agent and at least one anti-inflammatory agent; the microspheres thus do not release the at least one analgesic agent and at least one anti-inflammatory agent until they have been released from the gel. For example, a gel may be deployed around a target tissue site (e.g., a nerve root). Dispersed within the gel are a plurality of microspheres that encapsulate the desired therapeutic agent. Certain of these microspheres degrade once released from the gel, thus releasing the at least one analgesic agent and at least one anti-inflammatory agent. The analgesic agents and anti-inflammatory agents may be placed into separate microspheres and then the microspheres combined, or the active ingredients can first be combined and then placed into the microspheres together.

Microspheres, much like a fluid, may disperse relatively quickly, depending upon the surrounding tissue type, and hence disperse the at least one analgesic agent and at least one anti-inflammatory agent. In some embodiments, the diameter of the microspheres range from about 10 microns in diameter to about 200 microns in diameter. In some embodiments they range from about 20 to 120 microns in diameters. Methods for making microspheres include but are not limited to solvent evaporation, phase separation and fluidized bed coating. In some situations, this may be desirable; in others, it may be more desirable to keep the at least one analgesic agent and at least one anti-inflammatory agent tightly constrained to a well-defined target site.

The present invention also contemplates the use of adherent gels to so constrain dispersal of the therapeutic agent. These gels may be deployed, for example, in a disc space, in a spinal canal, or in surrounding tissue.

Cannulas and Needles

It will be appreciated by those with skill in the art that the depot can be administered to the target site using a "cannula" or "needle" that can be a part of a drug delivery device e.g., a syringe, a gun drug delivery device, or any medical device suitable for the application of a drug to a targeted organ or anatomic region. The cannula or needle of the drug depot device is designed to cause minimal physical and psychological trauma to the patient.

Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. In various embodiments, the cannula or needle may be inserted using a transforaminal approach in the spinal foramen space, for example, along an inflamed nerve root and the drug depot implanted at this site for treating the condition. Typically, the transforaminal approach involves approaching the intervertebral space through the intervertebral foramina.

Some examples of lengths of the cannula or needle may include, but are not limited to, from about 50 to 150 mm in length, for example, about 65 mm for epidural pediatric use, about 85 mm for a standard adult and about 110 mm for an obese adult patient. The thickness of the cannula or needle will also depend on the site of implantation. In various embodiments, the thickness includes, but is not limited to, from about 0.05 to about 1.655. The gauge of the cannula or needle may be the widest or smallest diameter or a diameter in between for insertion into a human or animal body. The widest diameter is typically about 14 gauge, while the smallest diameter is about 25 gauge. In various embodiments the gauge of the needle or cannula is about 18 to about 22 gauge.

In various embodiments, like the drug depot and/or gel, the cannula or needle includes dose radiographic markers that indicate location at or near the site beneath the skin, so that the user may accurately position the depot at or near the site using any of the numerous diagnostic imaging procedures. Such diagnostic imaging procedures include, for example, X-ray imaging or fluoroscopy. Examples of such radiographic markers include, but are not limited to, barium, calcium phosphate, and/or metal beads or particles.

In various embodiments, the needle or cannula may include a transparent or translucent portion that can be visualizable by ultrasound, fluoroscopy, x-ray, or other imaging techniques. In such embodiments, the transparent or translucent portion may include a radiopaque material or ultrasound responsive topography that increases the contrast of the needle or cannula relative to the absence of the material or topography.

Sterilization

The drug depot, and/or medical device to administer the drug may be sterilizable. In various embodiments, one or more components of the drug depot, and/or medical device to administer the drug are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the drug depot is included in a gel.

Other methods may also be used to sterilize the depot and/or one or more components of the device, including, but not limited to, gas sterilization, such as, for example, with ethylene oxide or steam sterilization.

Kits

In various embodiments, a kit is provided comprising a plurality of implantable drug depots useful for reducing, preventing or treating pain and inflammation in a patient in need of such treatment, the kit comprising a first set of the plurality of drug depots capable of releasing a therapeutically effective bolus dose of an analgesic and/or an anti-inflammatory agent or pharmaceutically acceptable salts thereof at a site beneath the skin and a second set of the plurality of drug depots capable of releasing a therapeutically effective amount of the analgesic and the anti-inflammatory agent or pharmaceutically acceptable salts thereof over a period of at least three days.

The kit may include additional parts along with the drug depot and/or medical device combined together to be used to implant the drug depots (e.g., pellets, gel, etc.). The kit may include the drug depot device in a first compartment. The second compartment may include a canister holding the drug depots or each drug depot with a different release profile may be labeled and placed in a different compartment (e.g., bolus dose depot compartment, sustained release depot compartment, etc.) and any other instruments needed for the localized drug delivery. A third compartment may include gloves, drapes, wound dressings and other procedural supplies for maintaining sterility of the implanting process, as well as an instruction booklet. A fourth compartment may include additional cannulas and/or needles. Each tool may be separately packaged in a plastic pouch that is radiation sterilized. A fifth compartment may include an agent for radiographic imaging. A cover of the kit may include illustrations of the implanting procedure and a clear plastic cover may be placed over the compartments to maintain sterility.

Administration

In various embodiments, the analgesic agent and the anti-inflammatory agent may be parenterally administered. The term "parenteral" as used herein refers to modes of administration, which bypass the gastrointestinal tract, and include for example, intravenous, intramuscular, continuous or intermittent infusion, intraperitoneal, intrasternal, subcutaneous, intra-operatively, intrathecally, intradiskally, peridiskally, epidurally, perispinally, intraarticular injection or combinations thereof.

Parenteral administration may additionally include, for example, an infusion pump that administers a pharmaceutical composition (e.g., analgesic and anti-inflammatory combination) through a catheter near the spine or one or more inflamed joints, an implantable mini-pump that can be inserted at or near the target site, an implantable controlled release device or sustained release delivery system that can release a certain amount of the composition per hour or in intermittent bolus doses. One example of a suitable pump for use is the SynchroMed® (Medtronic, Minneapolis, Minn.) pump. This pump has three sealed chambers. One contains an electronic module and battery. The second contains a peristaltic pump and drug reservoir. The third contains an inert gas, which provides the pressure needed to force the pharmaceutical composition into the peristaltic pump. To fill the pump, the pharmaceutical composition is injected through the reservoir fill port to the expandable reservoir. The inert gas creates pressure on the reservoir, and the pressure forces the pharmaceutical composition through a filter and into the pump chamber. The pharmaceutical composition is then pumped out of the device from the pump chamber and into the catheter, which will direct it for deposit at the target site. The rate of delivery of pharmaceutical composition is controlled by a microprocessor. This allows the pump to be used to deliver similar or different amounts of pharmaceutical composition continuously, at specific times, or at set intervals between deliveries.

Potential drug delivery devices suitable for adaptation for the methods described herein include but are not limited to those described, for example, in U.S. Pat. No. 6,551,290 (assigned to Medtronic, the entire disclosure is herein incorporated by reference), which describes a medical catheter for target specific drug delivery; U.S. Pat. No. 6,571,125 (assigned to Medtronic, the entire disclosure is herein incorporated by reference), which describes an implantable medical device for controllably releasing a biologically active agent; U.S. Pat. No. 6,594,880 (assigned to Medtronic, the entire disclosure is herein incorporated by reference), which describes an intraparenchymal infusion catheter system for delivering therapeutic agents to selected sites in an organism; and U.S. Pat. No. 5,752,930 (assigned to Medtronic, the entire disclosure is herein incorporated by reference), which describes an implantable catheter for infusing equal volumes of agents to spaced sites. In various embodiments, pumps may be adapted with a pre-programmable implantable apparatus with a feedback regulated delivery, a micro-reservoir osmotic release system for controlled release of chemicals, small, light-weight devices for delivering liquid medication, implantable microminiature infusion devices, implantable ceramic valve pump assemblies, or implantable infusion pumps with a collapsible fluid chamber. Alzet® osmotic pumps (Durect Corporation, Cupertino, Calif.) are also available in a variety of sizes, pumping rates, and durations suitable for use in the described methods. In various embodiments, a method for delivering a therapeutic agent at or near the target tissue site of a patient is provided. The method comprising inserting a cannula at or near a target tissue site and implanting the drug depot at the target site beneath the skin of the patient and brushing, dripping, injecting, or painting the gel in the target site to hold or have the drug depot adhere to the target site. In this way unwanted migration of the drug depot away from the target site is reduced or eliminated.

In various embodiments, because the combination of analgesic and anti-inflammatory agent is locally administered, therapeutically effective doses may be less than doses administered by other routes (oral, topical, etc.). In turn, systemic side effects, such as for example, liver transaminase elevations, hepatitis, liver failure, myopathy, constipation, etc. may be reduced or eliminated.

In various embodiments, to administer the gel having the drug depot dispersed therein to the desired site, first the cannula or needle can be inserted through the skin and soft tissue down to the target tissue site and the gel administered (e.g., brushed, dripped, injected, or painted, etc.) at or near the target site. In those embodiments where the drug depot is separate from the gel, first the cannula or needle can be inserted through the skin and soft tissue down to the site of injection and one or more base layer(s) of gel can be administered to the target site. Following administration of the one or more base layer(s), the drug depot can be implanted on or in the base layer(s) so that the gel can hold the depot in place or reduce migration. If required a subsequent layer or layers of gel can be applied on the drug depot to surround the depot and further hold it in place. Alternatively, the drug depot may be implanted first and then the gel placed (e.g., brushed, dripped, injected, or painted, etc.) around the drug depot to hold it in place. By using the gel, accurate and precise implantation of a drug depot can be accomplished with minimal physical and psychological trauma to the patient. The gel also avoids the need to suture the drug depot to the target site reducing physical and psychological trauma to the patient.

In various embodiments, when the target site comprises a spinal region, a portion of fluid (e.g., spinal fluid, etc.) can be withdrawn from the target site through the cannula or needle first and then the depot administered (e.g., placed, dripped, injected, or implanted, etc.). The target site will re-hydrate (e.g., replenishment of fluid) and this aqueous environment will cause the drug to be released from the depot.

Figure 4:
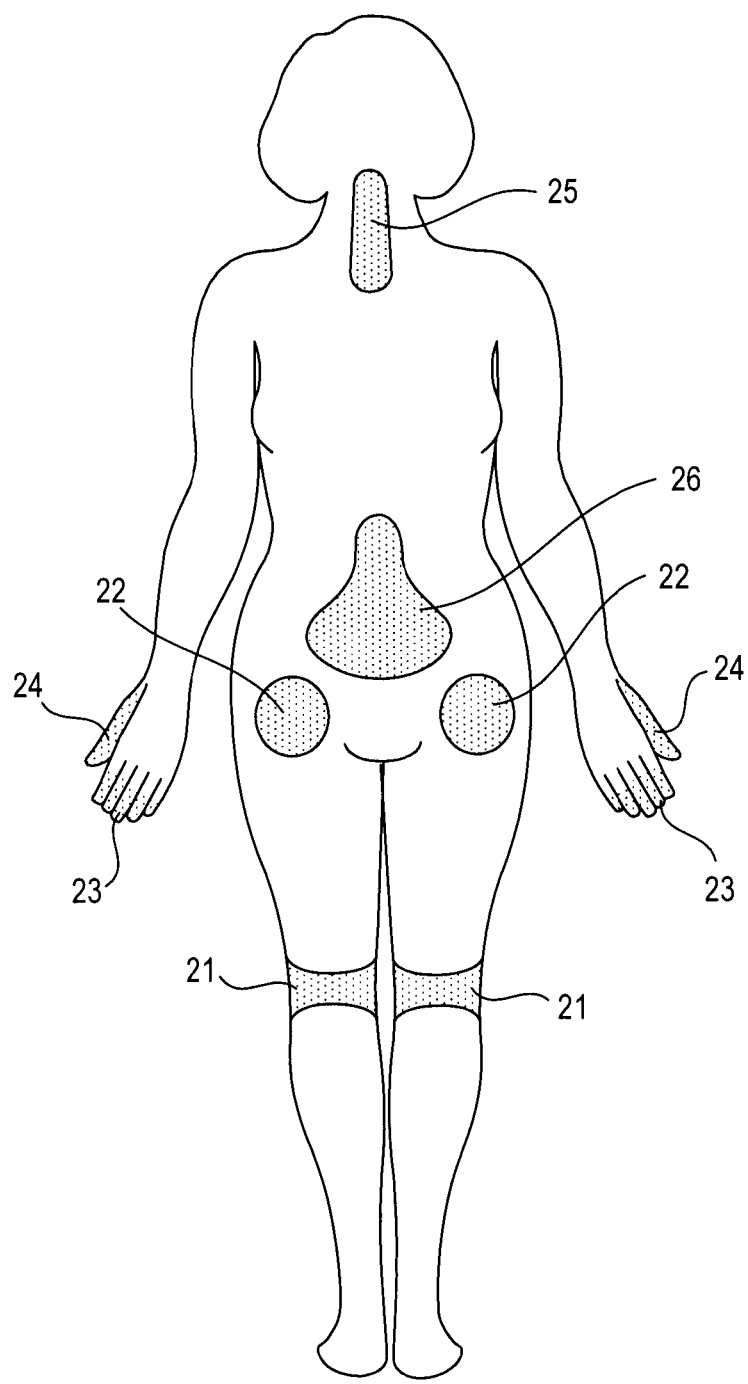
FIG. 4 illustrates a number of common locations within a patient that may be sites at which inflammation and/or pain occurs and locations at which the drug depot containing at least one analgesic agent and at least one anti-inflammatory agent can be administered locally thereto.

FIG. 4 illustrates a number of common locations within a patient that may be sites at which inflammation and/or pain may occur. It will be recognized that the locations illustrated in FIG. 4 are merely exemplary of the many different locations within a patient that may be the sites of inflammation and/or pain. For example, inflammation and/or pain may occur at a patient's knees 21, hips 22, fingers 23, thumbs 24, neck 25, and spine 26.

Figure 5:
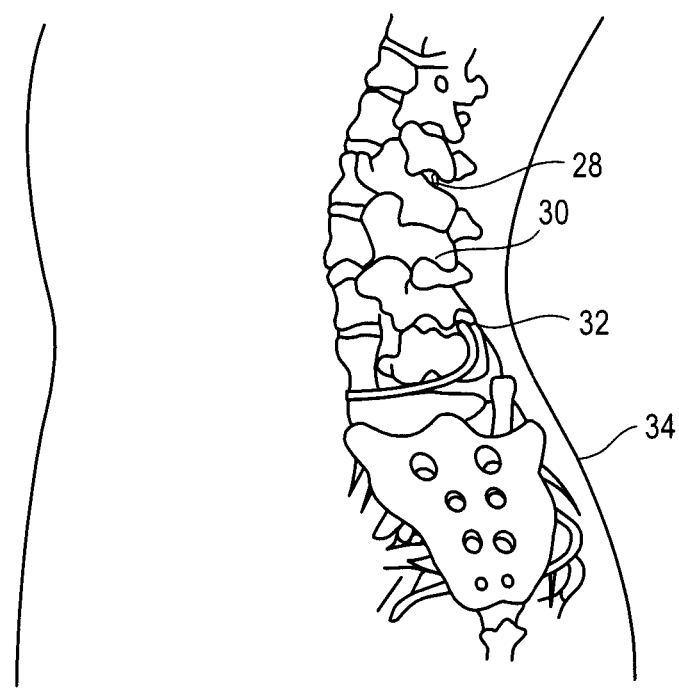
FIG. 5 illustrates a schematic dorsal view of the spine and sites where the drug depot containing at least one analgesic agent and at least one anti-inflammatory agent can be administered locally thereto.

One exemplary embodiment where the depot is suitable for use in pain management due to inflammation is illustrated in FIG. 5. Schematically shown in FIG. 5 is a dorsal view of the spine and sites where the drug depot may be inserted using a cannula or needle beneath the skin 34 to a spinal site 32 (e.g., spinal disc space, spinal canal, soft tissue surrounding the spine, nerve root, etc.) and one or more drug depots 28 and 32 are delivered to various sites along the spine. In this way, when several drug depots are to be implanted, they are implanted in a manner that optimizes location, accurate spacing, and drug distribution.

Although the spinal site is shown, as described above, the drug depot can be delivered to any site beneath the skin, including, but not limited to, at least one muscle, ligament, tendon, cartilage, spinal disc, spinal foraminal space, near the spinal nerve root, or spinal canal.

The at least one analgesic agent and at least one anti-inflammatory agent-based formulation may be used to form different pharmaceutical preparations (e.g., drug depots, injectable formulations, etc.). The pharmaceutical preparations may be formed in an administration with a suitable pharmaceutical carrier that may be solid or liquid, and placed in the appropriate form for parenteral or other administration as desired. As persons of ordinary skill are aware, known carriers include but are not limited to water, gelatin, lactose, starches, stearic acid, magnesium stearate, sicaryl alcohol, talc, vegetable oils, benzyl alcohols, gums, waxes, propylene glycol, polyalkylene glycols and other known carriers.

Another embodiment provides a method for treating a mammal suffering from inflammation and/or pain, said method comprising administering a therapeutically effective amount of at least one analgesic agent and at least one anti-inflammatory agent at a target site beneath the skin at or near the target site. The at least one analgesic agent and at least one anti-inflammatory agent may for example be administered locally to the target tissue site as a drug depot.

In some embodiments, the therapeutically effective dosage amount and the release rate profile are sufficient to reduce inflammation and/or pain for a period of at least one day, for example, 1-90 days, 1-10 days, 1-3 days, 3-7 days, 3-12 days; 3-14 days, 7-10 days, 7-14 days, 7-21 days, 7-30 days, 7-50 days, 7-90 days, 7-140 days, or 14-140 days.

In some embodiments the at least one analgesic agent and at least one anti-inflammatory agent or a portion of the at least one analgesic agent and at least one anti-inflammatory agent are administered as a bolus dose at the target tissue to provide an immediate release of the at least one analgesic agent and at least one anti-inflammatory agent.

In some embodiments there is a composition useful for the treatment of inflammation comprising an effective amount of at least one analgesic agent and at least one anti-inflammatory agent that is capable of being administered to e.g., a pain or inflammatory site. By way of example, they may be administered locally to the foraminal spine, the epidural space or the intrathecal space of a spinal cord. Exemplary administration routes include but are not limited to catheter drug pumps, one or more local injections, polymer releases or combinations thereof.

In some embodiments, the at least one analgesic agent and at least one anti-inflammatory agent are administered parenterally, e.g., by injection. In some embodiments, the injection is intrathecal, which refers to an injection into the spinal canal (intrathecal space surrounding the spinal cord). An injection may also be into a muscle or other tissue. In other embodiments, the analgesic agent and the anti-inflammatory agent is administered by placement into an open patient cavity during surgery.

In some embodiments, the formulation is implantable at or near a target tissue site at the time of surgery. The active ingredients may then be released from the depot via diffusion in a sustained fashion over a period of time, e.g., 3-15 days, 5-10 days or 7-10 days post surgery in order to address pain and inflammation.

In some embodiments, a desired release profile is maintained for at least three days, at least ten days, at least twenty days, at least thirty days, at least forty days, at least fifty days, at least ninety days, at least one hundred days, at least one-hundred and thirty-five days, at least one-hundred and fifty days, or at least one hundred and eighty days.

In some embodiments, the drug depot may release 5%, 10%, 15%, 20%, 25%, 30%, 40%, 50%, 60%, 70%, 80%, 90%, 95%, or 99% of the at least one analgesic agent or pharmaceutically acceptable salt thereof and at least one anti-inflammatory agent or pharmaceutically acceptable salt thereof relative to a total amount of at least one analgesic agent or pharmaceutically acceptable salt thereof and at least one anti-inflammatory agent loaded in the drug depot over a period of at least three days, at least seven days, at least ten days, at least twenty days, at least thirty days, at least forty days, at least fifty days, at least ninety days, at least one hundred days, at least one-hundred and thirty-five days, at least one-hundred and fifty days, or at least one hundred and eighty days. In various embodiments, the analgesic will be released in an initial burst dose, then the analgesic will be released daily for 3 days and then stop (e.g., this will be suitable to reduce, prevent or treat, post-operative pain), while the anti-inflammatory agent will be released daily without a burst dose for 3 to 12 days, 5 to 10 days or 7 to 10 days after the drug depot is administered to the target tissue site.

In various embodiments, an implantable drug depot useful for reducing, preventing or treating pain and inflammation is provided in a patient in need of such treatment, the implantable drug depot comprising a therapeutically effective amount of an analgesic and an anti-inflammatory agent or pharmaceutically acceptable salts thereof, the depot being implantable at a site beneath the skin to reduce, prevent or treat pain and/or inflammation, wherein the drug depot (i) comprises one or more immediate release layer(s) that is capable of releasing about 5% to about 20% of the analgesic and the anti-inflammatory agent or pharmaceutically acceptable salts thereof relative to a total amount of the analgesic and the anti-inflammatory agent or pharmaceutically acceptable salts thereof loaded in the drug depot over a first period of up to 48 hours and (ii) one or more sustain release layer(s) that is capable of releasing about 21% to about 99% of the analgesic and the anti-inflammatory agent or pharmaceutically acceptable salts thereof relative to a total amount of the analgesic and the anti-inflammatory agent or pharmaceutically acceptable salts thereof loaded in the drug depot over a subsequent period of up to 3 days to 6 months or 3 days to 2 weeks.

By way of non-limiting example, the target tissue site may comprise at least one muscle, ligament, tendon, cartilage, spinal disc, spinal foraminal space near the spinal nerve root, facet or spinal canal. The target tissue may be associated with an acute disease or chronic disease or surgery.

In some embodiments, the at least one analgesic agent or pharmaceutically acceptable salt thereof and at least one anti-inflammatory agent or pharmaceutically acceptable salt thereof is encapsulated in a plurality of depots comprising microparticles, microspheres, microcapsules, and/or microfibers suspended in a gel.

In some embodiments, an implantable drug depot is provided, wherein the drug depot (i) comprises one or more immediate release layer(s) that releases a bolus dose of at least one analgesic agent or pharmaceutically acceptable salt thereof and at least one anti-inflammatory agent or pharmaceutically acceptable salt thereof at a site beneath the skin and (ii) one or more sustain release layer(s) that releases an effective amount of at least one analgesic agent or pharmaceutically acceptable salt thereof and at least one anti-inflammatory agent or pharmaceutically acceptable salt thereof over a period of 3 days to 6 months. By way of example, in the drug depot, the one or more immediate release layer(s) may comprise poly (lactide-co-glycolide) (PLGA) and the one or more sustain release layer(s) may comprise polylactide (PLA).

Method of Making

In various embodiments, the drug depot comprising the active ingredients can be made by combining a biocompatible polymer and a therapeutically effective amount of the active ingredients or pharmaceutically acceptable salts thereof and forming the implantable drug depot from the combination.

Various techniques are available for forming at least a portion of a drug depot from the biocompatible polymer(s), therapeutic agent(s), and optional materials, including solution processing techniques and/or thermoplastic processing techniques. Where solution processing techniques are used, a solvent system is typically selected that contains one or more solvent species. The solvent system is generally a good solvent for at least one component of interest, for example, biocompatible polymer and/or therapeutic agent. The particular solvent species that make up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up the depot to obtain the desired release rate and desired thickness.

In various embodiments, a solution containing solvent and biocompatible polymer are combined and placed in a mold of the desired size and shape. In this way, polymeric regions, including barrier layers, lubricious layers, and so forth can be formed. If desired, the solution can further comprise, one or more of the following: other therapeutic agent(s) and other optional additives such as radiographic agent(s), etc. in dissolved or dispersed form. This results in a polymeric matrix region containing these species after solvent removal. In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming the depot or portions thereof include molding techniques (for example, injection molding, rotational molding, and so forth), extrusion techniques (for example, extrusion, co-extrusion, multi-layer extrusion, and so forth) and casting.

Thermoplastic processing in accordance with various embodiments comprises mixing or compounding, in one or more stages, the biocompatible polymer(s) and one or more of the following: the active ingredients, optional additional therapeutic agent(s), radiographic agent(s), and so forth. The resulting mixture is then shaped into an implantable drug depot. The mixing and shaping operations may be performed using any of the conventional devices known in the art for such purposes.

During thermoplastic processing, there exists the potential for the therapeutic agent(s) to degrade, for example, due to elevated temperatures and/or mechanical shear that are associated with such processing. For example, certain therapeutic agents may undergo substantial degradation under ordinary thermoplastic processing conditions. Hence, processing is preferably performed under modified conditions, which prevent the substantial degradation of the therapeutic agent(s). Although it is understood that some degradation may be unavoidable during thermoplastic processing, degradation is generally limited to 10% or less. Among the processing conditions that may be controlled during processing to avoid substantial degradation of the therapeutic agent(s) are temperature, applied shear rate, applied shear stress, residence time of the mixture containing the therapeutic agent, and the technique by which the polymeric material and the therapeutic agent(s) are mixed.

Mixing or compounding biocompatible polymer with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), inactive ingredients, etc.) to form a mixture. A common way of doing so is to apply mechanical shear to a mixture of the biocompatible polymer(s) and additive(s). Devices in which the biocompatible polymer(s) and additive(s) may be mixed in this fashion include devices such as single screw extruders, twin screw extruders, banbury mixers, high-speed mixers, ross kettles, and so forth.

Any of the biocompatible polymer(s) and various additives may be premixed prior to a final thermoplastic mixing and shaping process, if desired (e.g., to prevent substantial degradation of the therapeutic agent among other reasons).

For example, in various embodiments, a biocompatible polymer is precompounded with a radiographic agent (e.g., radio-opacifying agent) under conditions of temperature and mechanical shear that would result in substantial degradation of the therapeutic agent, if it were present. This precompounded material is then mixed with therapeutic agent under conditions of lower temperature and mechanical shear, and the resulting mixture is shaped into the active ingredient containing drug depot. Conversely, in another embodiment, the biocompatible polymer can be precompounded with the therapeutic agent under conditions of reduced temperature and mechanical shear. This precompounded material is then mixed with, for example, a radio-opacifying agent, also under conditions of reduced temperature and mechanical shear, and the resulting mixture is shaped into the drug depot.

The conditions used to achieve a mixture of the biocompatible polymer and therapeutic agent and other additives will depend on a number of factors including, for example, the specific biocompatible polymer(s) and additive(s) used, as well as the type of mixing device used.

As an example, different biocompatible polymers will typically soften to facilitate mixing at different temperatures. For instance, where a depot is formed comprising PLGA or PLA polymer, a radio-opacifying agent (e.g., bismuth subcarbonate), and a therapeutic agent prone to degradation by heat and/or mechanical shear (e.g., clonidine), in various embodiments, the PGLA or PLA can be premixed with the radio-opacifying agent at temperatures of about, for example, 150° C. to 170° C. The therapeutic agent is then combined with the premixed composition and subjected to further thermoplastic processing at conditions of temperature and mechanical shear that are substantially lower than is typical for PGLA or PLA compositions. For example, where extruders are used, barrel temperature, volumetric output are typically controlled to limit the shear and therefore to prevent substantial degradation of the therapeutic agent(s). For instance, the therapeutic agent and premixed composition can be mixed/compounded using a twin screw extruder at substantially lower temperatures (e.g., 100-105° C.), and using substantially reduced volumetric output (e.g., less than 30% of full capacity, which generally corresponds to a volumetric output of less than 200 cc/min). It is noted that this processing temperature is well below the melting points of certain active ingredients, such as an anti-inflammatory and analgesic because processing at or above these temperatures will result in substantial therapeutic agent degradation. It is further noted that in certain embodiments, the processing temperature will be below the melting point of all bioactive compounds within the composition, including the therapeutic agent. After compounding, the resulting depot is shaped into the desired form, also under conditions of reduced temperature and shear.

In other embodiments, biodegradable polymer(s) and one or more therapeutic agents are premixed using non-thermoplastic techniques. For example, the biocompatible polymer can be dissolved in a solvent system containing one or more solvent species. Any desired agents (for example, a radio-opacifying agent, a therapeutic agent, or both radio-opacifying agent and therapeutic agent) can also be dissolved or dispersed in the solvents system. Solvent is then removed from the resulting solution/dispersion, forming a solid material. The resulting solid material can then be granulated for further thermoplastic processing (for example, extrusion) if desired.

As another example, the therapeutic agent can be dissolved or dispersed in a solvent system, which is then applied to a pre-existing drug depot (the pre-existing drug depot can be formed using a variety of techniques including solution and thermoplastic processing techniques, and it can comprise a variety of additives including a radio-opacifying agent and/or viscosity enhancing agent), whereupon the therapeutic agent is imbibed on or in the drug depot. As above, the resulting solid material can then be granulated for further processing, if desired.

Typically, an extrusion processes may be used to form the drug depot comprising a biocompatible polymer(s), therapeutic agent(s) and radio-opacifying agent(s). Co-extrusion may also be employed, which is a shaping process that can be used to produce a drug depot comprising the same or different layers or regions (for example, a structure comprising one or more polymeric matrix layers or regions that have permeability to fluids to allow immediate and/or sustained drug release). Multi-region depots can also be formed by other processing and shaping techniques such as co-injection or sequential injection molding technology.

In various embodiments, the depot that may emerge from the thermoplastic processing (e.g., pellet, strip, etc.) is cooled. Examples of cooling processes include air cooling and/or immersion in a cooling bath. In some embodiments, a water bath is used to cool the extruded depot. However, where a water-soluble therapeutic agent such as active ingredients are used, the immersion time should be held to a minimum to avoid unnecessary loss of therapeutic agent into the bath.

In various embodiments, immediate removal of water or moisture by use of ambient or warm air jets after exiting the bath will also prevent re-crystallization of the drug on the depot surface, thus controlling or minimizing a high drug dose "initial burst" or "bolus dose" upon implantation or insertion if this is release profile is not desired. Thus, a sustained release region of the drug depot may, in various embodiments, be made by immediately removal of water or moisture.

In various embodiments, the drug depot can be prepared by mixing or spraying the drug with the polymer and then molding the depot to the desired shape. In various embodiments, active ingredients are used and mixed or sprayed with the PLGA or PEG550 polymer, and the resulting depot may be formed by extrusion and dried.

The drug depot may also comprise combining a biocompatible polymer and a therapeutically effective amount of at least one analgesic agent or pharmaceutically acceptable salt thereof and at least one anti-inflammatory agent or pharmaceutically acceptable salt thereof and forming the implantable drug depot from the combination.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A plurality of implantable drug depots useful for reducing, preventing or treating pain and/or inflammation in a patient in need of such treatment, the plurality of drug depots comprising a first set of one or more drug depots capable of releasing a therapeutically effective bolus dose of an analgesic and/or an anti-inflammatory agent or pharmaceutically acceptable salts thereof at a site beneath the skin and a second set of one or more drug depots capable of releasing a therapeutically effective amount of the analgesic and/or the anti-inflammatory agent or pharmaceutically acceptable salts thereof over a period of at least three days, the first set of one or more drug depots and the second set of one or more drug depots being solid and separate from each other and the second set of one or more drug depots comprises a polymer having an average molecular weight of between about 10,000 to 100,000, wherein the analgesic comprises alfentanil, butorphanol, codeine, fentanyl, hydromorphone, levorphanol, meperidine, morphine, sufentanil, tramadol or a combination thereof, and the anti-inflammatory agent comprises clonidine, fluocinolone, dexamethasone, sulindac, sulfasalazine or a combination thereof, and
wherein each depot of the first and second set comprises a pore forming agent that is dextrose in an amount of less than 20% of the weight of the polymer, and each depot of the first and second set comprises an adherent gel comprising a polyethylene glycol (PEG) conjugate or a PEG viscosity enhancing agent, wherein the gel stiffens after delivery to a target site having a pre-dosed modulus of elasticity of about $1 \times 10^4$ to about $3 \times 10^5$ dynes/cm$^2$ and a post-dosed modulus of elasticity of about $1 \times 10^5$ to about $7 \times 10^5$ dynes/cm$^2$.

2. A plurality of implantable drug depots according to claim 1, wherein at least one of the second set of drug depot releases the analgesic and/or an anti-inflammatory over a period of 3 days to 6 months.

3. A plurality of implantable drug depots according to claim 1, wherein at least one of the second set of drug depot releases the analgesic and/or an anti-inflammatory over a period of 3 days to 2 weeks.

4. A plurality of implantable drug depots according to claim 1, wherein the one or more drug depots of the first set releases a bolus dose of an analgesic and anti-inflammatory agent.

5. A plurality of implantable drug depots according to claim 1, wherein the first and second set of the drug depots further comprise one or more polymer layers containing the analgesic and/or the anti-inflammatory agent.

6. A plurality of implantable drug depots according to claim 1, wherein each drug depot of the first and second sets further comprises at least one biodegradable polymer comprising one or more of poly(lactide-co-glycolide) (PLGA), polylactide (PLA), polyglycolide (PGA), D-lactide, D,L-lactide, L-lactide, D,L-lactide-ε-caprolactone, D,L-lactide-glycolide-ε-caprolactone caprolactone, glycolide-caprolactone, poly(glycolide-,-caprolactone) or a combination thereof.

7. A plurality of implantable drug depots according to claim 1, wherein each drug depot of the first or second set further comprises a polymer and the polymer comprises about 20 wt % to about 90 wt % of the drug depot.

8. A plurality of implantable drug depots according to claim 1, wherein at least one drug depot releases about 20% to about 99% of the analgesic and/or the anti-inflammatory agent or pharmaceutically acceptable salts thereof relative to a total amount of the analgesic and/or the anti-inflammatory agent or pharmaceutically acceptable salts thereof loaded in the drug depot over a period of 3 days to 6 months after the drug depot is administered to a target tissue site.

9. A plurality of implantable drug depots according to claim 1, wherein the analgesic and/or the anti-inflammatory agent or pharmaceutically acceptable salts thereof are encapsulated in each drug depot as microspheres, microcapsules, and/or microfibers suspended in the gel.

10. A plurality of implantable drug depots according to claim 1, wherein each drug depot is in the form of one or more pellets.

11. A kit comprising a plurality of implantable drug depots useful for reducing, preventing or treating pain and/or inflammation in a patient in need of such treatment, the kit comprising:
an adherent gel that is part of a two-component delivery system and when the two components are mixed, a chemical process is activated to form the gel and cause the gel to adhere to the target tissue;
a first set of the plurality of drug depots capable of releasing a therapeutically effective bolus dose of an analgesic and/or an anti-inflammatory agent or pharmaceutically acceptable salts thereof at a site beneath the skin; and
a second set of the plurality of drug depots capable of releasing a therapeutically effective amount of the analgesic and/or the anti-inflammatory agent or pharmaceutically acceptable salts thereof over a period of at least three days, the first set of one or more drug depots and the second set of one or more drug depots being solid and separate from each other and the second set of one or more drug depots comprises a polymer having an average molecular weight of between about 10,000 to 100,000, wherein the analgesic comprises alfentanil, butorphanol, codeine, fentanyl, hydromorphone, levorphanol, meperidine, morphine, sufentanil, tramadol or a combination thereof, and the anti-inflammatory agent comprises clonidine, fluocinolone, dexamethasone, sulindac, sulfasalazine or a combination thereof, and
wherein each depot of the first and second set comprises a pore forming agent that is dextrose in an amount of less than 20% of the weight of the polymer and the adherent gel comprises a polyethylene glycol (PEG) conjugate or a PEG viscosity enhancing agent, wherein the gel stiffens after delivery to a target site having a pre-dosed modulus of elasticity of about $1 \times 10^4$ to about $3 \times 10^5$ dynes/cm$^2$ and a post-dosed modulus of elasticity of about $1 \times 10^5$ to about $7 \times 10^5$.

12. A kit according to claim 11, wherein the second set of the plurality of drug depots releases the analgesic and/or an anti-inflammatory over a period of 3 days to 6 months.

13. A kit according to claim 11, wherein the second set of the plurality of drug depots releases the analgesic and/or an anti-inflammatory over a period of 3 days to 2 weeks.

14. A kit according to claim 11, wherein the first set of the plurality of drug depots releases a bolus amount of analgesic.

15. A kit according to claim 11, wherein the first set of the plurality of drug depots releases a bolus amount of anti-inflammatory agent.

16. A plurality of implantable drug depots according to claim 1, wherein the pre-dosed modulus of elasticity is about $5 \times 10^4$ to about $1 \times 10^5$ dynes/cm$^2$ and the post-dosed modulus of elasticity is about $2 \times 10^5$ to about $5 \times 10^5$ dynes/cm$^2$.

* * * * *